(12) United States Patent
Honda et al.

(10) Patent No.: US 11,666,373 B2
(45) Date of Patent: Jun. 6, 2023

(54) TREATMENT SYSTEM AND ENERGY TREATMENT TOOL

(71) Applicant: Olympus Corporation, Hachioji (JP)

(72) Inventors: Yoshitaka Honda, Hachioji (JP); Yuki Kawaguchi, Koshu (JP)

(73) Assignee: OLYMPUS CORPORATION, Tokyo (JP)

( * ) Notice: Subject to any disclaimer, the term of this patent is extended or adjusted under 35 U.S.C. 154(b) by 712 days.

(21) Appl. No.: 16/663,731

(22) Filed: Oct. 25, 2019

(65) Prior Publication Data

US 2020/0054388 A1    Feb. 20, 2020

Related U.S. Application Data

(63) Continuation of application No. PCT/JP2017/017016, filed on Apr. 28, 2017.

(51) Int. Cl.
*A61B 18/14* (2006.01)
*A61B 18/00* (2006.01)
(Continued)

(52) U.S. Cl.
CPC ...... *A61B 18/1442* (2013.01); *A61B 18/1445* (2013.01); *A61B 2017/00973* (2013.01);
(Continued)

(58) Field of Classification Search
CPC ............ A61B 18/1442; A61B 18/1445; A61B 18/1447; A61B 2018/145;
(Continued)

(56) References Cited

U.S. PATENT DOCUMENTS

| 6,270,497 B1 * | 8/2001 | Sekino | A61B 18/14 606/49 |
| 2003/0004507 A1 * | 1/2003 | Francischelli | A61B 18/1206 606/41 |

(Continued)

FOREIGN PATENT DOCUMENTS

| JP | 2012-196340 A | 10/2012 |
| JP | 2016-154908 A | 9/2016 |

(Continued)

OTHER PUBLICATIONS

Oct. 29, 2019 International Preliminary Report on Patentability issued in International Application No. PCT/JP2017/017016.
(Continued)

*Primary Examiner* — Linda C Dvorak
*Assistant Examiner* — Nicholas S Borsch
(74) *Attorney, Agent, or Firm* — Oliff PLC

(57) ABSTRACT

A treatment system includes an energy treatment tool and a power supply device. The energy treatment tool includes respective first and second grasps configured to be coupled with one another and are capable of pivoting with respect to one another so as to grip a treatment target therebetween. A plurality of bipolar electrodes is attached to the respective first and second grasps. The plurality of bipolar electrodes receives a high-frequency current to flow through the treatment target so as to develop a first temperature distribution in the treatment target. A treatment energy source is configured to be coupled to one of the respective first and second grasps and receives electric energy to generate treatment energy different from the high-frequency current and to apply the generated treatment energy to the treatment target so as to develop a second temperature distribution in the treatment target.

14 Claims, 18 Drawing Sheets

(51) Int. Cl.
*A61B 18/12* (2006.01)
*A61B 17/00* (2006.01)
(52) U.S. Cl.
CPC ............ *A61B 2018/0063* (2013.01); *A61B 2018/0072* (2013.01); *A61B 2018/00601* (2013.01); *A61B 2018/00702* (2013.01); *A61B 2018/00714* (2013.01); *A61B 2018/00958* (2013.01); *A61B 2018/126* (2013.01); *A61B 2018/1467* (2013.01)
(58) Field of Classification Search
CPC .... A61B 2018/1452; A61B 2018/1455; A61B 2018/1457; A61B 2018/1462; A61B 18/085; A61B 2018/087
See application file for complete search history.

(56) References Cited

U.S. PATENT DOCUMENTS

| | | | | |
|---|---|---|---|---|
| 2003/0065327 | A1* | 4/2003 | Wellman | A61B 18/1482 606/51 |
| 2013/0253508 | A1* | 9/2013 | Ide | A61B 18/14 606/41 |
| 2013/0338665 | A1 | 12/2013 | Tanaka et al. | |
| 2016/0310207 | A1 | 10/2016 | Honda et al. | |
| 2017/0172643 | A1 | 6/2017 | Takashino et al. | |
| 2017/0224406 | A1 | 8/2017 | Takei et al. | |
| 2017/0245923 | A1 | 8/2017 | Takashino et al. | |
| 2017/0252087 | A1 | 9/2017 | Takashino et al. | |

FOREIGN PATENT DOCUMENTS

| | | |
|---|---|---|
| WO | 2013/088892 A1 | 6/2013 |
| WO | 2016/035470 A1 | 3/2016 |
| WO | 2016/080147 A1 | 5/2016 |
| WO | 2016/167196 A1 | 10/2016 |
| WO | 2017/018205 A1 | 2/2017 |

OTHER PUBLICATIONS

Jul. 25, 2017 International Search Report issued in International Application No. PCT/JP2017/017016.

* cited by examiner

TREATMENT SYSTEM AND ENERGY TREATMENT TOOL

CROSS-REFERENCE TO RELATED APPLICATION

This application is a continuation application of PCT Application No. PCT/JP 2017/017016 filed on Apr. 28, 2017, which is hereby incorporated by reference in its entirety.

TECHNICAL FIELD

The disclosed technology relates generally to a treatment system and, more particularly, some embodiments relate to an energy treatment tool for treating a treatment target gripped between a pair of grasps by applying treatment energy to the treatment target. The treatment system incorporates the energy treatment tool.

DESCRIPTION OF THE RELATED ART

WO2016/080147A1 discloses an energy treatment tool for gripping a treatment target between a pair of grasps and applying treatment energy to the gripped treatment target. The disclosed energy treatment tool includes electrodes disposed respectively on the grasps. A bipolar electrode includes two electrodes. When the bipolar electrode is supplied with high-frequency electric power, the electrodes develop respective potentials that are different from each other, causing a high-frequency current to flow through the treatment target therebetween. One of the grasps incorporates a heater therein. When the heater is supplied with electric energy, i.e., heater electric power, the heater generates heater heat as treatment energy different from the high-frequency current. The heater heat is applied from the one of the grasps to the treatment target.

In a treatment using the energy treatment tool disclosed in WO2016/080147A1, a high-frequency current and treatment energy such as heater heat or the like that is different from the high-frequency current are simultaneously applied to a gripped treatment garget such as a blood vessel or the like, sealing the treatment target. It has been desired to stabilize the quality of a sealed treatment target.

BRIEF SUMMARY OF EMBODIMENTS

The disclosed technology has been made in view of the foregoing.

One aspect of the disclosed technology is directed to a treatment system having respective first and second grasps configured to be coupled with one another and are capable of pivoting with respect to one another so as to grip a treatment target therebetween. A plurality of bipolar electrodes is attached to the respective first and second grasps. The plurality of bipolar electrodes receives high-frequency electric power in a form of a high-frequency current to flow through the treatment target so as to develop a first temperature distribution in the treatment target. A treatment energy source is configured to be coupled to at least one of the respective first and second grasps. The treatment energy source receives electric energy to generate treatment energy different from the high-frequency current and to apply the generated treatment energy to the treatment target so as to develop a second temperature distribution in the treatment target. A processor configured to control transmissions of the respective high-frequency electric power and the electric energy to the respective plurality of bipolar electrodes and the treatment energy source and to switch to a sealing mode and a incising mode. The plurality of bipolar electrodes and the treatment energy source are capable of: in the sealing mode, simultaneously applying the high-frequency current and the treatment energy to the treatment target such that a first area having a relatively high temperature in the first temperature distribution overlaps a second area having a relatively low temperature in the second temperature distribution. And in the incising mode, simultaneously applying the high-frequency current and the treatment energy to the treatment target such that a third area having a relatively high temperature in the first temperature distribution overlaps a fourth area having a relatively high temperature in the second temperature distribution.

Another aspect of the disclosed technology is directed to an energy treatment tool used in a treatment system having respective first and second grasps configured to be coupled with one another and are capable of pivoting with respect to one another so as to grip a treatment target therebetween. A plurality of bipolar electrodes is attached to the respective first and second grasps. The plurality of bipolar electrodes receives high-frequency electric power in a form of a high-frequency current to flow through the treatment target so as to develop a first temperature distribution in the treatment target. At least one treatment energy source is configured to be coupled to one of the respective first and second grasps. The at least one treatment energy source receives electric energy to generate treatment energy different from the high-frequency current and to apply the generated treatment energy to the treatment target so as to develop a second temperature distribution in the treatment target. The plurality of bipolar electrodes and the treatment energy source are capable of: in a sealing mode, simultaneously applying the high-frequency current and the treatment energy to the treatment target such that a first area having a relatively high temperature in the first temperature distribution overlaps a second area having a relatively low temperature in the second temperature distribution. And in an incising mode, simultaneously applying the high-frequency current and the treatment energy to the treatment target such that a third area having a relatively high temperature in the first temperature distribution overlaps a fourth area having a relatively low temperature in the second temperature distribution.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of the disclosed technology to provide an energy treatment tool that stabilizes the quality of a sealed treatment target. Another object of the disclosed technology is to provide a treatment system that incorporates such an energy treatment tool.

First Embodiment

Figure 1:
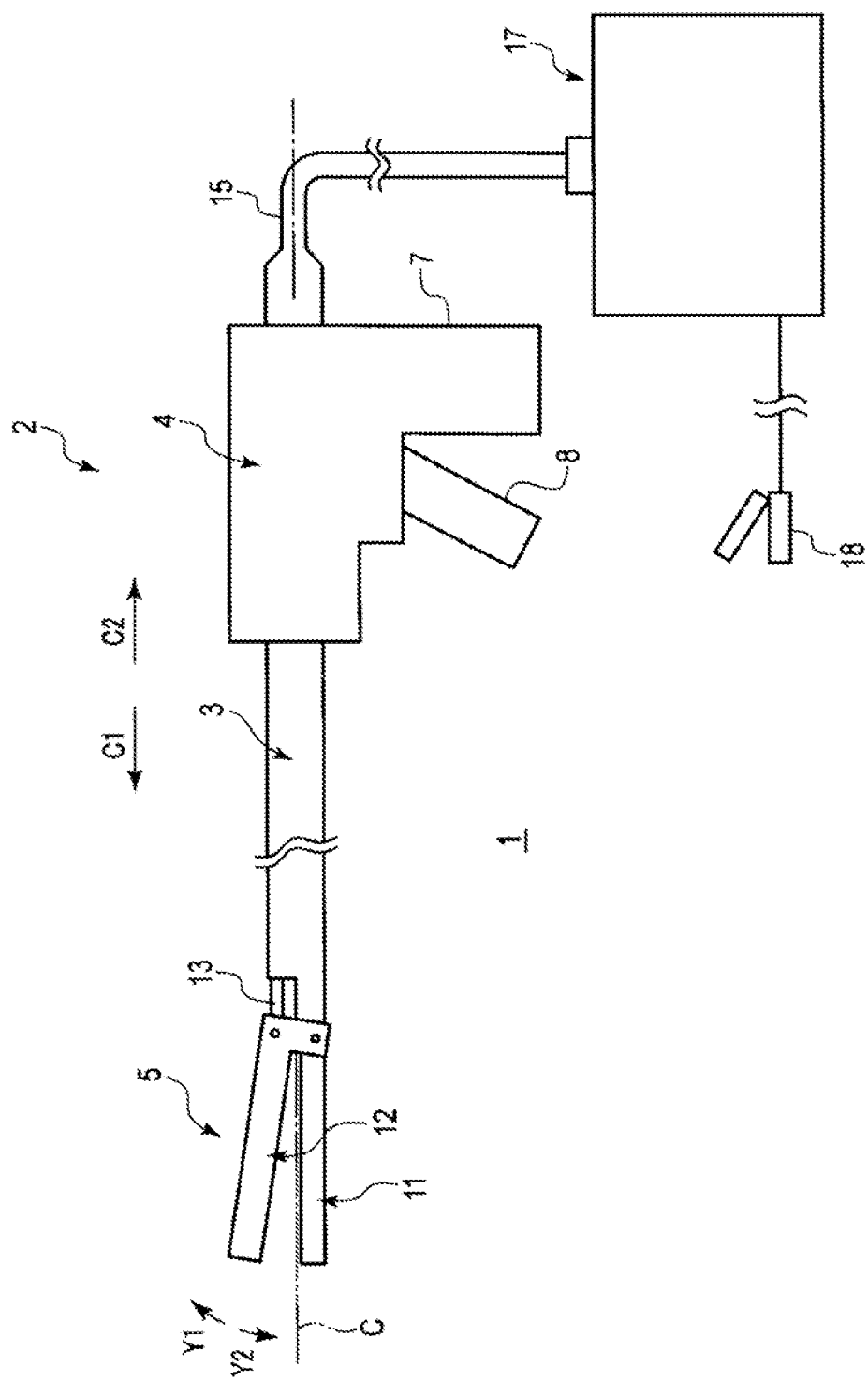
FIG. 1 is a schematic view illustrating a treatment system incorporating an energy treatment tool according to a first embodiment.

A first embodiment of the disclosed technology will be described hereinafter with reference to FIGS. 1 through 7. FIG. 1 is a view illustrating a treatment system 1 incorporating an energy treatment tool 2 according to the present embodiment. As illustrated in FIG. 1, the energy treatment tool 2 includes a shaft 3, a housing 4, and an end effector 5. The shaft 3 has a longitudinal axis C as a central axis thereof and extends along the longitudinal axis C. One side in a direction along the longitudinal axis C will be referred to as a distal-end side, i.e., a direction C1 side, whereas the opposite side to the distal-end side as a proximal-end side, e.g., a direction C2 side. The housing 4 is coupled to the proximal-end side of the shaft 3. The end effector 5 is disposed on the distal-end portion of the shaft 3.

The housing 4 includes a grip 7 extending in a direction across the longitudinal axis C. A handle 8 is angularly movably attached to the housing 4. When the handle 8 is angularly moved with respect to the housing 4, the handle 8 is opened or closed with respect to the grip 7. The end effector 5 includes a pair of grasps, i.e., jaws 11 and 12. According to an example, one of the grasps 11 and 12 is integrally formed with the shaft 3 or fixed to the shaft 3, whereas the other of the grasps 11 and 12 is angularly movably attached to the shaft 3. According to another example, both the grasps 11 and 12 are movably attached to the shaft 3. According to still another example, a rod member, not illustrated, extends through the shaft 3 and projects from a distal end of the shaft 3 toward the distal-end side. The portion of the rod member that projects from the shaft 3 functions as one of the grasps 11 and 12. The other of the grasps 11 and 12 is angularly movably attached to the shaft 3.

A movable member 13 that is disposed inside or outside of the shaft 3 extends from the proximal-end side to distal-end side thereof. The movable member 13 has a distal end portion connected to the end effector 5. The movable member 13 has a proximal-end portion coupled to the handle 8 in the housing 4. When the handle 8 is opened or closed with respect to the grip 7, the movable member 13 moves along the longitudinal axis C. At least one of the grasps 11 and 12 is thus angularly moved with respect to the shaft 3, opening or closing the space between the grasps 11 and 12. Since the space between the grasps 11 and 12 is openable and closable, a treatment target such as a biotissue or the like can be gripped between the grasps 11 and 12. Directions in which the end effector 5 is opened and closed, respectively, i.e., directions indicated by an arrow Y1 and an arrow Y2, extend across, i.e., substantially perpendicularly to, the longitudinal axis C.

A cable 15 has an end connected to the housing 4 of the energy treatment tool 2. The other end of the cable 15 is connected to a power supply device 17 separate from the energy treatment tool 2. The treatment system 1 that incorporates the energy treatment tool 2 includes an operating member 18. According to the example illustrated in FIG. 1, the operating member 18 is a foot switch separate from the energy treatment tool 2 and is electrically connected to the power supply device 17. Based on an operation made on the operating member 18, the power supply device 17 supplies electric energy to the energy treatment tool 2. While in an output power state suitable for sealing a treatment target, i.e., in a sealing mode, the operating member 18 is able to enter an operation for outputting electric energy to the energy treatment tool 2. While in an output power state suitable for incising a treatment target, i.e., in an incising mode, the operating member 18 is able to enter an operation for outputting electric energy to the energy treatment tool 2. According to an example, the operating member 18 includes an operating button or the like mounted on the housing 4, instead of or in addition to the foot switch.

Figure 2:
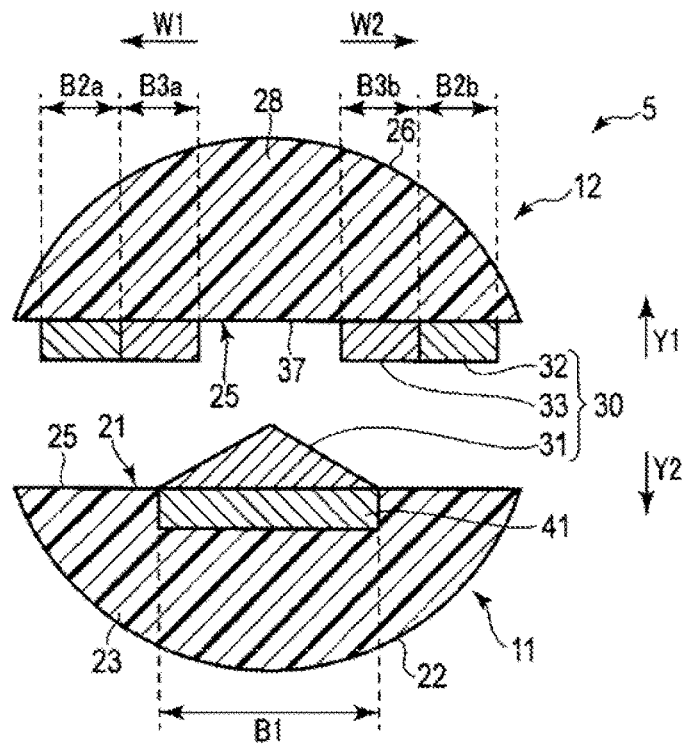
FIG. 2 is a schematic view illustrating a cross section of an end effector according to the first embodiment, taken along a plane substantially perpendicular to directions along a longitudinal axis thereof.

FIG. 2 is a view illustrating a cross section of the end effector 5, taken along a plane substantially perpendicular to directions along the longitudinal axis C. There are defined herein widthwise directions, i.e., directions indicated by an arrow W1 and an arrow W2, of the end effector 5, extending across, i.e., substantially perpendicularly to, directions along the longitudinal axis C and also across, i.e., substantially perpendicularly to, the directions in which the end effector 5 is opened and closed, respectively. As illustrated in FIG. 2, the grasp 11 includes a gripping surface 21 facing the grasp 12 and a rear surface 22 facing away from the gripping surface 21. The grasp 12 includes a gripping surface 25 facing the grasp 11, i.e., the gripping surface 21, and a rear surface 26 facing away from the gripping surface 25.

The grasp 11 includes a support body 23, and the grasp 12 includes a support body 28. Each of the support bodies 23 and 28 has at least a surface made of a material that is electrically insulative. The support body 23 extends continuously from the proximal-end portion to distal-end portion of the grasp 11 in a direction along the longitudinal axis C. The support body 23 defines the rear surface 22 of the grasp 11 and also defines a portion of the gripping surface 21. The support body 28 extends continuously from the proximal-end portion to distal-end portion of the grasp 12 in a direction along the longitudinal axis C. The support body 28 defines the rear surface 26 of the grasp 12 and also defines a portion of the gripping surface 25.

A first electrode 31 is disposed on the grasp 11, and a second electrode 32 and a third electrode 33 are disposed on the grasp 12. The first electrode 31 defines a portion of the gripping surface 21 of the grasp 11. Each of the second electrode 32 and the third electrode 33 defines a portion of the gripping surface 25 of the grasp 12. Each of the first through third electrodes 31 through 33 is made of an electrically conductive material that is highly thermally conductive. The bipolar electrode 30 includes the first through third electrodes 31 through 33 of the end effector 5. When high-frequency electric power is supplied as electric energy to the bipolar electrode 30, a high-frequency current flows through a treatment target gripped between the grasps 11 and 12. The high-frequency current is thus applied as treatment energy to the treatment target. According to the present embodiment, the grasp 11 with the first electrode 31 disposed thereon is referred to as a first grasp, whereas the grasp 12 with the second electrode 32 disposed thereon is referred to as a second grasp.

According to the present embodiment, the first electrode 31 extends continuously from the proximal-end portion to distal-end portion of the grasp 11 in a direction along the longitudinal axis C. Each of the second electrode 32 and the third electrode 33 extends continuously from the proximal-end portion to distal-end portion of the grasp 12 in a direction along the longitudinal axis C. The first through third electrodes 31 through 33 extend over respective ranges that are substantially the same as each other in the direction along the longitudinal axis C. Therefore, the dimensions of the first through third electrodes 31 through 33 in the direction along the longitudinal axis C are substantially the same as each other.

The first electrode 31 is disposed on the gripping surface 21 at a central portion thereof in widthwise directions of the end effector 5. The gripping surface 21 includes an insulative facing surface 35 lying outwardly of the first electrode 31 in the widthwise directions of the end effector 5. The insulative facing surface 35 is defined by the surface of the support body 23 and is electrically insulative. The insulative facing surface 35 is also appropriately thermally resistant. The insulative facing surface 35 is disposed on each of the both sides of the first electrode 31 in the widthwise directions of the end effector 5.

The gripping surface 25 includes a bearing surface 37 at a central portion thereof in the widthwise directions of the end effector 5. The bearing surface 37 is defined by the surface of the support body 28 and is electrically insulative. The bearing surface 37 is also appropriately thermally resistant. The third electrode 33 on the gripping surface 25 is disposed outwardly of the bearing surface 37 in the widthwise directions of the end effector 5. According to the present embodiment, the third electrode 33 is disposed adjacent to each of the both sides of the bearing surface 37 in the widthwise directions of the end effector 5. The second electrode 32 on the gripping surface 25 is disposed outwardly of the third electrode 33 in the widthwise directions of the end effector 5. According to the present embodiment, the second electrode 32 is disposed in a position spaced from the bearing surface 37 in the widthwise directions of the end effector 5. The second electrode 32 is disposed on each of the both sides of the bearing surface 37. A film-like member, not illustrated, that is electrically insulative is disposed between the second electrode 32 and the third electrode 33. Therefore, electric conduction is prevented from occurring between the second electrode 32 and the third electrode 33.

When the space between the grasps 11 and 12 is closed, the first electrode 31 on the grasp 11 can abut against the bearing surface 37 of the grasp 12. When the first electrode 31 abuts against the bearing surface 37, the first electrode 31 is spaced from the second electrode 32 and the third electrode 33 and kept out of contact with the second electrode 32 and the third electrode 33. Therefore, in the end effector 5, the first electrode 31 is effectively prevented from contacting the second electrode 32 and the third electrode 33.

According to the present embodiment, a dimension B1 of the first electrode 31 in the widthwise directions is larger than a dimension (B2$a$+B2$b$) of the second electrode 32 in the widthwise directions. Furthermore, the dimension B1 of the first electrode 31 in the widthwise directions is larger than a dimension (B3$a$+B3$b$) of the third electrode 33 in the widthwise directions. However, the dimension B1 of the first electrode 31 in the widthwise directions is smaller than sum (B2$a$+B2$b$+B3$a$+B3$b$) of the dimension (B2$a$+B2$b$) of the second electrode 32 in the widthwise directions and the dimension (B3$a$+B3$b$) of the third electrode 33 in the widthwise directions. As described hereinbefore, the dimensions of the first through third electrodes 31 through 33 in the direction along the longitudinal axis C are substantially the same as each other. Consequently, the surface area of the first electrode 31 is larger than the surface area of the second electrode 32 and larger than the surface area of the third electrode 33. The surface area of the first electrode 31 is smaller than the sum of the surface area of the second electrode 32 and the surface area of the third electrode 33.

According to the present embodiment, moreover, the grasp 11 as the first grasp includes a heater, i.e., heat generating body 41. The heater 41 functions as a treatment energy source, i.e., energy conversion element that, when supplied with electric energy, generates heater heat as another treatment energy than the high-frequency current. According to the present embodiment, the heater 41 is disposed in the grasp 11 at a central portion thereof in the widthwise directions of the end effector 5. The heater 41 is disposed on a rear surface 22 side of the first electrode 31. Heater heat generated by the heater 41 is transmitted to the first electrode 31, and is then applied from the first electrode 31 to the gripped treatment target. According to the present embodiment, therefore, heater heat as another treatment energy than the high-frequency current is applied from the grasp 11 to the treatment target.

Figure 3:
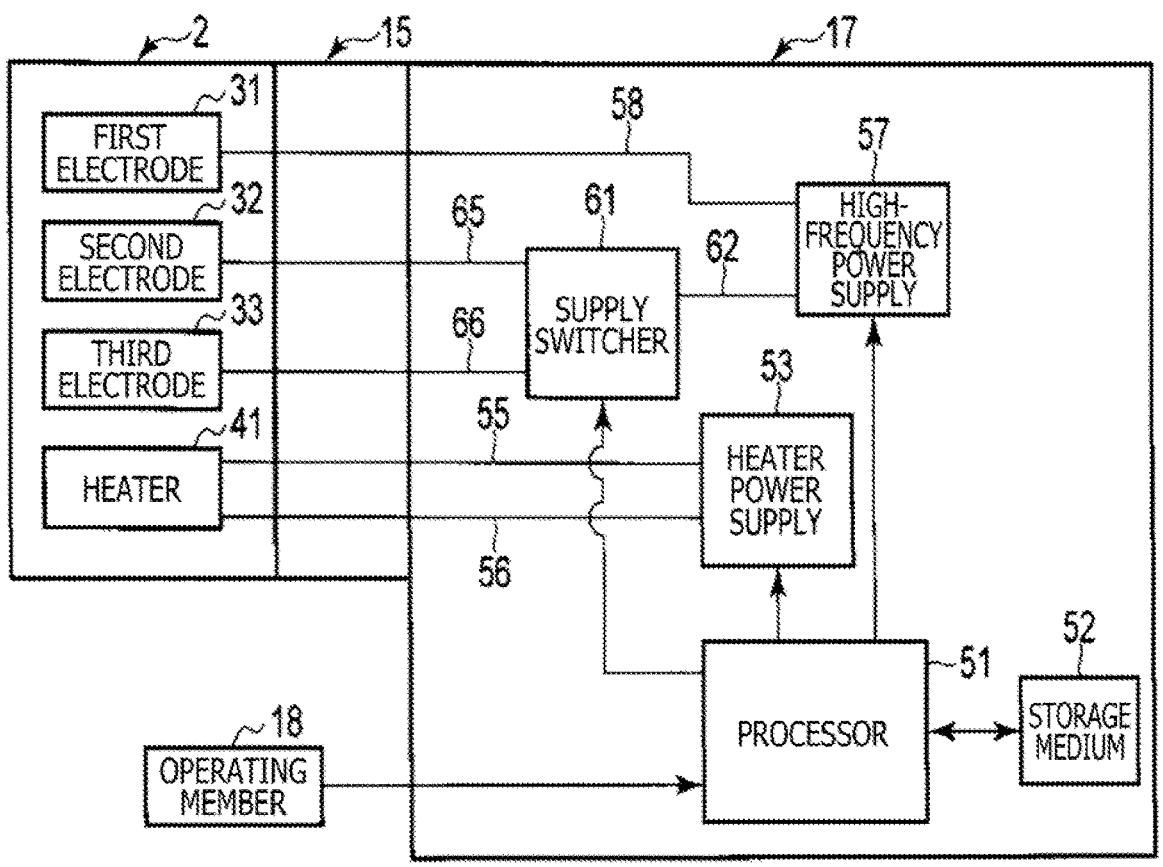
FIG. 3 is a block diagram schematically illustrating an arrangement for controlling the supply of high-frequency electric power to a bipolar electrode and the supply of electric energy to a heater according to the first embodiment.

FIG. 3 is a diagram illustrating an arrangement for controlling the supply of high-frequency electric power to the bipolar electrode 30 and the supply of electric energy to the heater 41. The power supply device 17 includes a processor, i.e., controller 51 and a storage medium 52. The processor 51 is constructed as an integrated circuit or the like including a central processing circuit (CPU), an application specific integrated circuit (ASIC), a field programmable gate array (FPGA), or the like. The processor 51 may be included as a single entity or a plurality of entities in the power supply device 17. The processor 51 performs its processing sequences according to programs stored in the processor 51 or the storage medium 52. The storage medium 52 stores therein processing programs used by the processor 51 and parameters, functions, tables, etc. used in the processing sequences performed by the processor 51. The processor 51 detects operation inputs entered from the operating member 18 such as a foot switch, etc.

The power supply device 17 includes a heater power supply 53. The heater power supply 53 includes a converter circuit, and a transformer, etc. The heater power supply 53 converts electric power from a battery power supply, an electric outlet power supply, or the like into electric energy to be supplied to the heater 41. The heater power supply 53 is electrically connected to the heater 41 by electric lines 55 and 56. Each of the electric lines 55 and 56 extends through the cable 15, the housing 4, and the shaft 3. The heater power supply 53 outputs the converted electric energy, i.e., heater electric power, thereby supplying it to the heater 41. At this time, direct current (DC) electric power or alternating current (AC) electric power is output as the electric energy. The processor 51 controls the output from the heater power supply 53 to control the supply of electric energy, i.e., heater electric power, to the heater 41.

Furthermore, the power supply device 17 includes a high-frequency power supply 57. The high-frequency power supply 57 includes a waveform generator, a converter circuit, a transformer, etc. The high-frequency power supply 57 converts electric power from a battery power supply, an electric outlet power supply, or the like into high-frequency electric power as electric energy to be supplied to the bipolar electrode 30. The high-frequency power supply 57 outputs the converted high-frequency electric power. The processor 51 controls the output from the high-frequency power supply 57. The high-frequency power supply 57 is electrically connected to the first electrode 31 through an electric line 58. The electric line 58 extends through the cable 15, the housing 4, and the shaft 3.

The power supply device 17 includes a supply switcher 61 in the form of a switch circuit or the like. The supply switcher 61 is electrically connected to the high-frequency power supply 57 through an electric line 62 in the power supply device 17. The supply switcher 61 is electrically connected to the second electrode 32 through an electric line 65, and also electrically connected to the third electrode 33 through an electric line 66. Each of the electric lines 65 and 66 extends through the cable 15, the housing 4, and the shaft 3. The processor 51 controls operation of the supply switcher 61.

The processor 51 controls the output from the high-frequency power supply 57 and operation of the supply switcher 61, thereby controlling the supply of high-frequency electric power to the bipolar electrode 30. According to the present embodiment, when the processor 51 controls operation of the supply switcher 61, the supply of high-frequency electric power to the bipolar electrode 30 is switched between a first supply state and a second supply state. When the supply of high-frequency electric power to the bipolar electrode 30 is switched between the first supply state and the second supply state, the state in which the high-frequency current is applied to the treatment target varies.

In the first supply state, the supply switcher 61 interrupts an electric connection between the electric line 66 and the electric line 62. In the first supply state, therefore, no high-frequency current flows through the third electrode 33 and the electric line 66, and the high-frequency electric power output from the high-frequency power supply 57 is not supplied to the third electrode 33. At this time, the high-frequency power supply 57 supplies the high-frequency electric power through the electric line 58 to the first electrode 31, and also supplies the high-frequency electric power through the electric lines 62 and 65 to the second electrode 32. In the first supply state, consequently, only the first electrode 31 and the second electrode 32 are supplied with the high-frequency electric power. In the first supply state, the first electrode 31 and the second electrode 32 develop respective potentials that are different from each other, causing a high-frequency current to flow through the treatment target gripped between the first electrode 31 and the second electrode 32.

In the second supply state, the supply switcher 61 electrically connects the electric line 66 and the electric line 62 to each other. In the second supply state, therefore, a high-frequency current flows through the third electrode 33 and the electric line 66, and the high-frequency electric power output from the high-frequency power supply 57 is supplied to the third electrode 33. At this time, the high-frequency power supply 57 supplies the high-frequency electric power through the electric line 58 to the first electrode 31, and also supplies the high-frequency electric power through the electric lines 62 and 65 to the second electrode 32. In the second supply state, consequently, all the first through third electrodes 31 through 33 are supplied with the high-frequency electric power. In the second supply state, the first electrode 31 develops a potential different from the second electrode 32 and the third electrode 33, and the second electrode 32 and the third electrode 33 develop respective potentials that are the same as each other. In the second supply state, a high-frequency current flows through the treatment target gripped between the first electrode 31 and the second and third electrodes 32 and 33.

The power supply device 17 may have a setting portion, not illustrated, such as a touch panel or the like. The setting portion makes it possible to set output levels of the heater power supply 53 respectively in the sealing mode and the incising mode and output levels of the high-frequency power supply 57 respectively in the sealing mode and the incising mode. The processor 51 controls the output from the heater power supply 53 and the output from the high-frequency power supply 57 based on the settings made by the setting portion.

Next, operation and advantages of the present embodiment will be described hereinafter. For performing a treatment using the energy treatment tool 2, the energy treatment tool 2 is connected through the cable 15 to the power supply device 17. Then, the surgeon holds the housing 4 and inserts the end effector 5 into a body cavity such as an abdominal cavity or the like. While a treatment target such as a blood vessel or the like is being positioned between the grasps 11 and 12, the surgeon closes the handle 8 on the grip 7. The grasps 11 and 12 are now closed, gripping the treatment target therebetween. With the treatment target gripped, the surgeon enters an operation through the operating member 18, causing the power supply device 17 to output electric energy to the energy treatment tool 2 in the sealing mode or the incising mode. Now, high-frequency electric power is supplied to the bipolar electrode 30, and electric energy is supplied to the heater 41.

When the high-frequency electric power is supplied to the bipolar electrode 30, a high-frequency current flows through the treatment target between the grasps 11 and 12 and is applied to the treatment target. When the high-frequency current is applied to the treatment target, there is developed in the treatment target a first temperature distribution due to the applied high-frequency current. When the electric energy is supplied to the heater 41, heater heat as another treatment energy than the high-frequency current is applied from the grasp 11 to the treatment target. When the heater heat is applied to the treatment target, the treatment target develops therein a second temperature distribution due to the heater heat, i.e., treatment energy.

Figure 4A:
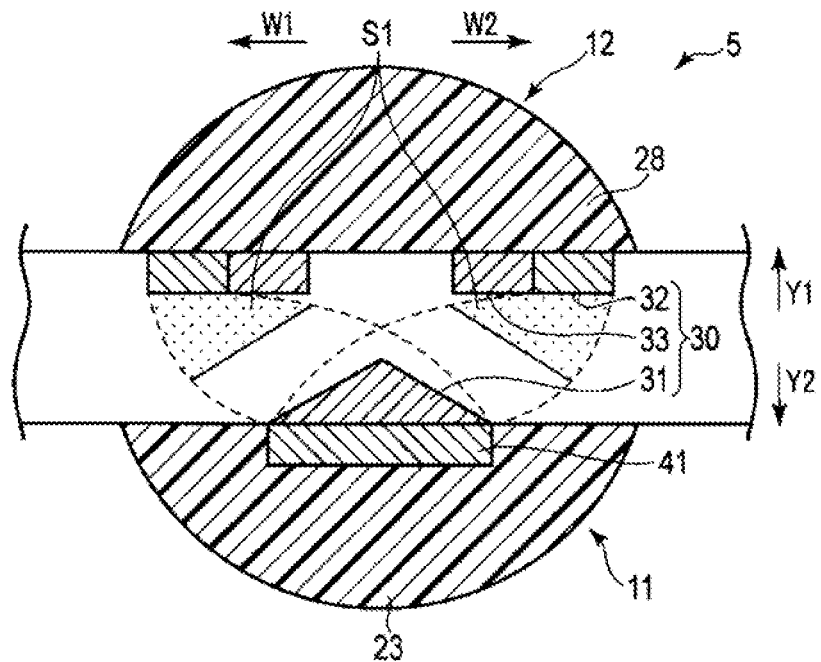
FIG. 4A is a schematic view illustrating by way of example a first temperature distribution developed in a treatment target while a power supply device according to the first embodiment is outputting power in a sealing mode.
Figure 4B:
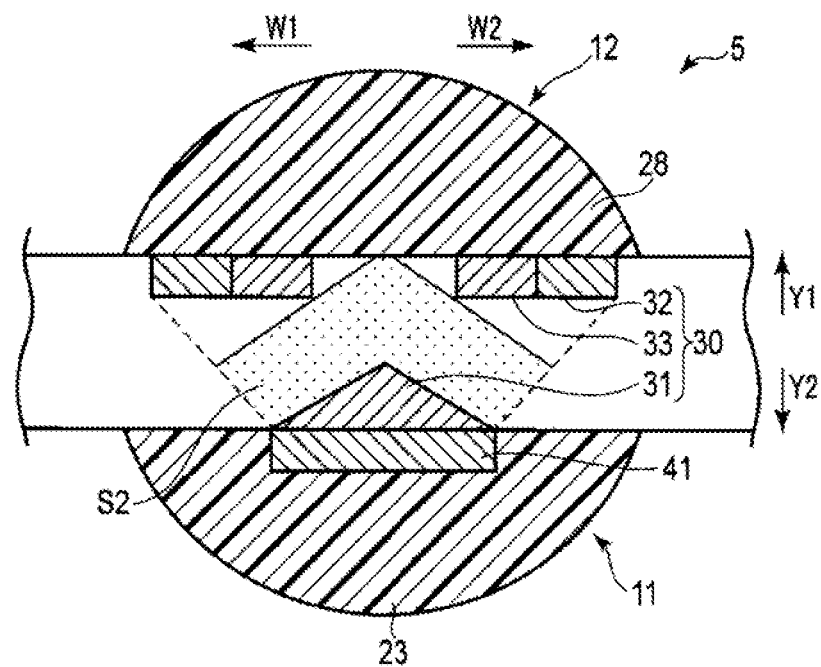
FIG. 4B is a schematic view illustrating by way of example a second temperature distribution developed in the treatment target while the power supply device according to the first embodiment is outputting power in the sealing mode.
Figure 5:
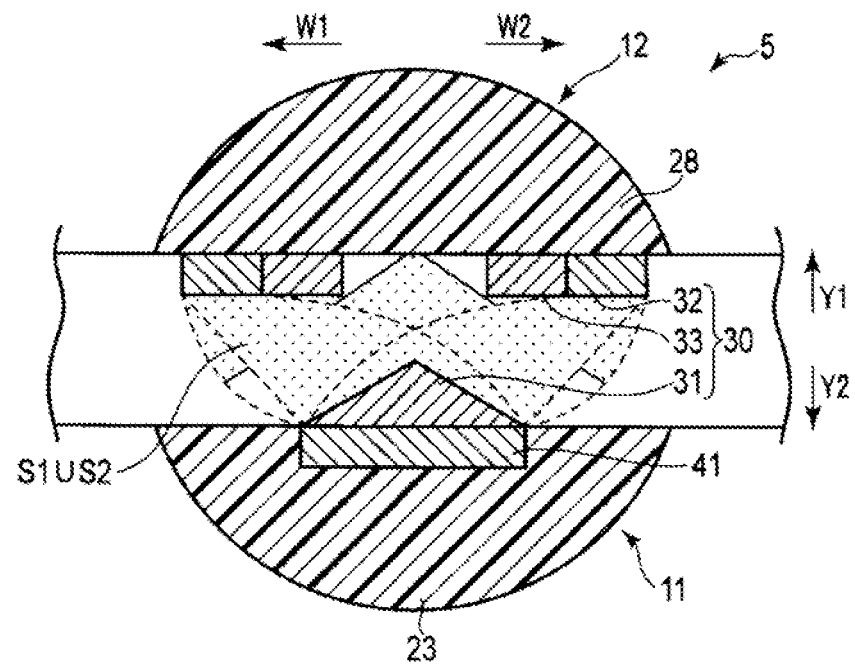
FIG. 5 is a schematic view illustrating by way of example a temperature distribution developed in the treatment target by both a high-frequency current and heater heat while the power supply device according to the first embodiment is outputting power in the sealing mode.
Figure 6A:
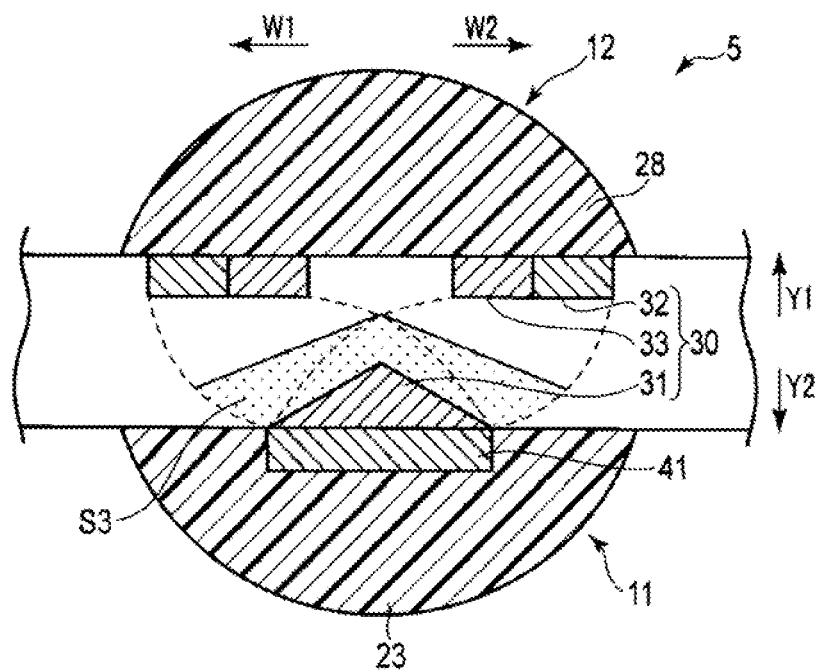
FIG. 6A is a schematic view illustrating by way of example a first temperature distribution developed in a treatment target while the power supply device according to the first embodiment is outputting power in an incising mode.
Figure 6B:
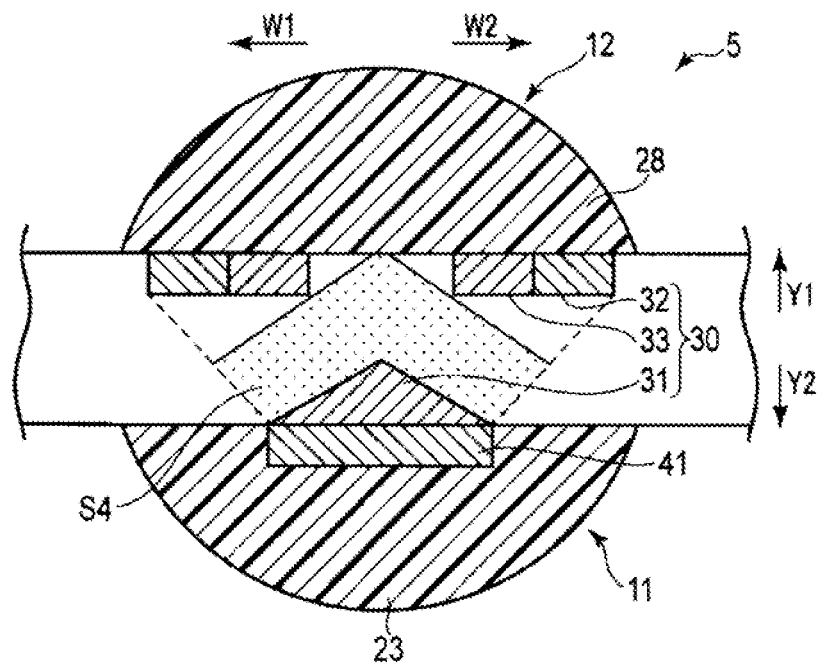
FIG. 6B is a schematic view illustrating by way of example a second temperature distribution developed in the treatment target while the power supply device according to the first embodiment is outputting power in the incising mode.
Figure 7:
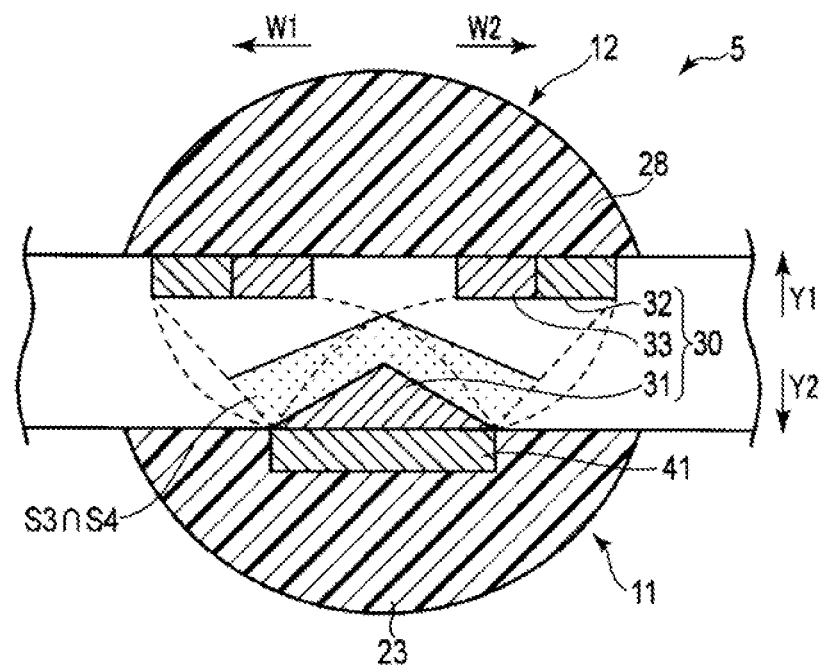
FIG. 7 is a schematic view illustrating by way of example a temperature distribution developed in the treatment target by both a high-frequency current and heater heat while the power supply device according to the first embodiment is outputting power in the incising mode.

FIG. 4A illustrates by way of example a first temperature distribution developed in the treatment target while the power supply device 17 is outputting power in the sealing mode. FIG. 4B illustrates by way of example a second temperature distribution developed in the treatment target while the power supply device 17 is outputting power in the sealing mode. FIG. 5 illustrates by way of example a temperature distribution developed in the treatment target by both a high-frequency current and heater heat while the power supply device 17 is outputting power in the sealing mode. The temperature distribution illustrated in FIG. 5 represents a combination of the first temperature distribution illustrated in FIG. 4A and the second temperature distribution illustrated in FIG. 4B. FIG. 6A illustrates by way of example a first temperature distribution developed in the treatment target while the power supply device 17 is outputting power in the incising mode. FIG. 6B illustrates by way of example a second temperature distribution developed in the treatment target while the power supply device 17 is outputting power in the incising mode. FIG. 7 illustrates by way of example a temperature distribution developed in the treatment target by both a high-frequency current and heater heat while the power supply device 17 is outputting power in the incising mode. The temperature distribution illustrated in FIG. 7 represents a combination of the first temperature distribution illustrated in FIG. 6A and the second temperature distribution illustrated in FIG. 6B.

In the sealing mode, the processor 51 controls operation of the supply switcher 61 thereby to supply high-frequency electric power to the bipolar electrode 30 in the first supply state. Therefore, no high-frequency electric power is supplied to the third electrode 33, but high-frequency electric power is supplied to only the first electrode 31 and the second electrode 32. In the sealing mode, consequently, a high-frequency current flows through the treatment target between the first electrode 31 and the second electrode 32, whereas no high-frequency current flows between the first electrode 31 and the third electrode 33.

As described hereinbefore, the surface area of the first electrode 31 is larger than the surface area of the second electrode 32. In the sealing mode, therefore, the area of the treatment target that is relatively close to the second electrode 32, i.e., the grasp 12, is an area where the current density of the high-frequency current is relatively high, and the area of the treatment target that is relatively close to the first electrode 31, i.e., the grasp 11, is an area where the current density of the high-frequency current is relatively low. According to the first temperature distribution due to the high-frequency current, the area where the current density of the high-frequency current is relatively high is an area where the temperature is relatively high. According to the first temperature distribution developed in the sealing mode, i.e., the first temperature distribution developed in the first supply state, as illustrated in FIG. 4A, an area S1 of the treatment target where the temperature is relatively high is positioned in an area relatively close to the second electrode 32, i.e., the grasp 12 as the second grasp, and the area of the treatment target where the temperature is relatively low is positioned in an area relatively close to the first electrode 31, i.e., the grasp 11 as the first grasp. In FIG. 4A, the area S1 where the temperature is relatively high is depicted stippled. In the area S1, the temperature goes higher toward the second electrode 32.

In the sealing mode, heater heat is transmitted from the heater 41 through the first electrode 31 to the treatment target. Therefore, the heater heat is applied from the grasp 11 as the first grasp to the treatment target. In the treatment target, the heater heat is transmitted from the grasp 11 side to the grasp 12 side. Therefore, as illustrated in FIG. 4B, according to the second temperature distribution developed in the sealing mode, an area S2 of the treatment target where the temperature is relatively high is positioned in an area relatively close to the first electrode 31, i.e., the grasp 11 as the first grasp, and the area of the treatment target where the temperature is relatively low is positioned in an area relatively close to the grasp 12 as the second grasp. In FIG. 4B, the area S2 where the temperature is relatively high is depicted stippled. In the area S2, the temperature goes higher toward the first electrode 31.

When in the sealing mode, i.e., when the high-frequency electric power is supplied to the bipolar electrode 30 in the first supply state, the first temperature distribution and the second temperature distribution are developed as described hereinbefore. Therefore, the area S1 where the temperature is relatively high according to the first temperature distribution is positioned in an area where the temperature is relatively low according to the second temperature distribution. In the sealing mode, the area S2 where the temperature is relatively high according to the second temperature distribution is positioned in an area where the temperature is relatively low according to the first temperature distribution. Consequently, while the high-frequency current and the heater heat are being simultaneously applied to the treatment target in the sealing mode, the low-temperature area according to the first temperature distribution is compensated for by the high-temperature area S2 according to the second temperature distribution, and the low-temperature area according to the second temperature distribution is compensated for by the high-temperature area S1 according to the first temperature distribution, thereby restraining an uneven temperature distribution in the treatment target between the first electrode 31 and the second electrode 32. Accordingly, the treatment target is prevented from developing temperature unevenness, and has its temperature uniformized or substantially uniformized in the range between the first electrode 31 and the second electrode 32. In the temperature distribution illustrated in FIG. 5, the range covering the high-temperature area S1 according to the first temperature distribution illustrated in FIG. 4A or the high-temperature area S2 according to the second temperature distribution illustrated in FIG. 4B is depicted stippled. In the sealing mode, actually, as indicated by the temperature distribution in FIG. 5, most of the treatment target gripped between the grasps 11 and 12 is in the range covering the high-temperature area S1 according to the first temperature distribution or the high-temperature area S2 according to the second temperature distribution. As described hereinbefore, using the energy treatment tool 2 according to the present embodiment, an uneven temperature distribution is restrained and the temperature distribution is uniformized in the treatment target between the first electrode 31 and the second electrode 32, compared with each of the case where only the first temperature distribution is developed and the case where only the second temperature distribution is developed. As the temperature of the treatment target is uniformized or substantially uniformized, the gripped treatment target can appropriately be modified in its entirety, resulting in an increased capability for sealing the treatment target such as a blood vessel or the like. As a consequence, the quality of the sealed treatment target is stabilized by using the energy treatment tool 2 according to the present embodiment.

In the incising mode, the processor 51 controls operation of the supply switcher 61 thereby to supply high-frequency electric power to the bipolar electrode 30 in the second supply state. Therefore, high-frequency electric power is supplied to all the first through third electrodes 31 through 33. When the second electrode 32 and the third electrode 33 are supplied with high-frequency electric power, the second electrode 32 and the third electrode 33 develop respective potentials that are the same as each other. In the incising mode, consequently, a high-frequency current flows through the treatment target between the first electrode 31 and the second electrode 32, and a high-frequency current also flows between the first electrode 31 and the third electrode 33.

As described hereinbefore, the surface area of the first electrode 31 is smaller than the sum of the surface area of the second electrode 32 and the surface area of the third electrode 33. In the incising mode, therefore, the area of the treatment target that is relatively close to the first electrode 31, i.e., the grasp 11, is an area where the current density of the high-frequency current is relatively high, and the area of the treatment target that is relatively close to the second electrode 32 and the third electrode 33, i.e., the grasp 12, is an area where the current density of the high-frequency current is relatively low. According to the first temperature distribution developed in the incising mode, i.e., the first temperature distribution developed in the second supply state, as illustrated in FIG. 6A, an area S3 of the treatment target where the temperature is relatively high is positioned in an area relatively close to the first electrode 31, i.e., the grasp 11 as the first grasp, and the area of the treatment target where the temperature is relatively low is positioned in an area relatively close to the second electrode 32 and the third electrode 33, i.e., the grasp 12 as the second grasp. In FIG. 6A, the area S3 where the temperature is relatively high is depicted stippled. In the area S3, the temperature goes higher toward the first electrode 31.

In the incising mode, heater heat is applied from the grasp 11 as the first grasp to the treatment target. In the treatment target, the heater heat is transmitted from the grasp 11 side to the grasp 12 side. Therefore, as illustrated in FIG. 6B, according to the second temperature distribution developed in the incising mode, as with the second temperature distribution developed in the sealing mode, an area S4 of the treatment target where the temperature is relatively high is positioned in an area relatively close to the first electrode 31, i.e., the grasp 11 as the first grasp, and the area of the treatment target where the temperature is relatively low is positioned in an area relatively close to the grasp 12 as the second grasp. However, in the incising mode, since the output from the heater power supply 53 is higher than in the sealing mode, the temperature of the heater 41 is higher. Therefore, the temperature of the treatment target is higher according to the second temperature distribution developed in the incising mode than according to the second temperature distribution developed in the sealing mode. In FIG. 6B, the area S4 where the temperature is relatively high is depicted stippled. In the area S4, the temperature goes higher toward the first electrode 31.

When in the incising mode, i.e., when the high-frequency electric power is supplied to the bipolar electrode 30 in the second supply state, the first temperature distribution and the second temperature distribution are developed as described hereinbefore. Therefore, the area S3 where the temperature is relatively high according to the first temperature distribution is positioned in the area S4 where the temperature is relatively high according to the second temperature distribution. In the incising mode, the area where the temperature is relatively low according to the second temperature distribution is positioned in an area where the temperature is relatively low according to the first temperature distribution. Consequently, while the high-frequency current and the heater heat are being simultaneously applied to the treatment target in the incising mode, the temperature is high in the local area of the treatment target that is relatively close to the first electrode 31, i.e., the grasp 11. In the temperature distribution illustrated in FIG. 7, the range shared by the high-temperature area S3 according to the first temperature distribution illustrated in FIG. 6A and the high-temperature area S4 according to the second temperature distribution illustrated in FIG. 6B is depicted stippled. In the incising mode, actually, as indicated by the temperature distribution in FIG. 7, only the portion of the treatment target gripped between the grasps 11 and 12 in the vicinity of the first electrode 31 is in the range shared by the high-temperature area S3 according to the first temperature distribution and the high-temperature area S4 according to the second temperature distribution. As the temperature of the local area of the treatment target that is relatively close to the first electrode 31 is high, the efficiency with which the treatment energy such as the heater heat, etc. is transmitted to the treatment target is increased, resulting in an increase in the speed at which the treatment target is incised. In the incising mode, therefore, the treatment target such as a blood vessel is incised quickly.

Modification of the First Embodiment

Figure 8:
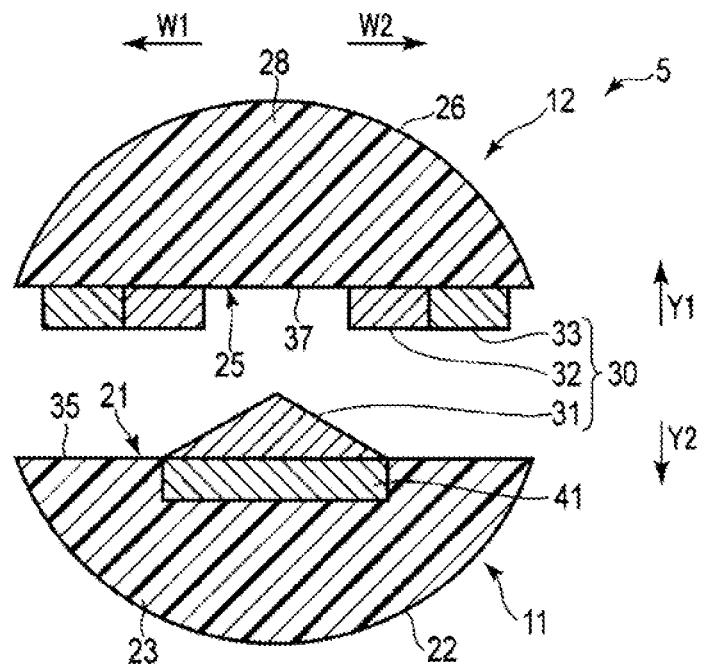
FIG. 8 is a schematic view illustrating a cross section of an end effector according to a modification of the first embodiment, taken along a plane substantially perpendicular to directions along a longitudinal axis thereof.

According to a modification illustrated in FIG. 8, on the gripping surface 25, the third electrode 33 is disposed outwardly of the second electrode 32 in the widthwise directions of the end effector 5. The second electrode 32 and the third electrode 33 are electrically insulated from each other. The surface areas of the first through third electrodes 31 through 33 are related to each other in the same manner as with the first embodiment. According to the present modification, in each of the sealing mode and the incising mode, the supply of high-frequency electric power to the bipolar electrode 30 and the supply of electric energy to the heater 41 are controlled by the processor 51 in the same manner as with the first embodiment.

In the present modification, according to the first temperature distribution developed in the sealing mode, the area where the temperature is relatively high is positioned in the area that is relatively close to the second electrode 32, i.e., the grasp 12 as the second grasp. According to the second temperature distribution developed in the sealing mode, the area where the temperature is relatively low is positioned in the area that is relatively close to the second electrode 32. According to the present modification, therefore, in the sealing mode, the area where the temperature is relatively high according to the first temperature distribution due to the high-frequency current is positioned in the area where the temperature is relatively low according to the second temperature distribution due to the heater heat. In the present modification, furthermore, according to the first temperature distribution developed in the incising mode, the area where the temperature is relatively high is positioned in the area that is relatively close to the first electrode 31, i.e., the grasp 11 as the first grasp. According to the second temperature distribution developed in the incising mode, the area where the temperature is relatively high is positioned in the area that is relatively close to the first electrode 31. According to the present modification, therefore, in the incising mode, the area where the temperature is relatively high according to the first temperature distribution is positioned in the area where the temperature is relatively high according to the second temperature distribution.

Consequently, the present modification operates in the same manner as and offers the same advantages as with the first embodiment. According to the present modification, the second electrode 32 is disposed inwardly of the third electrode 33 in the widthwise directions of the end effector 5. In the sealing mode, therefore, when a high-frequency current flows between the first electrode 31 and the second electrode 32, the high-frequency current is less likely to invade an area of a biotissue or the like that is disposed outwardly of a gripped treatment target in the widthwise directions. In the sealing mode, heat generated due to the high-frequency current is effectively prevented from invading the area of the biotissue or the like that is disposed outwardly of the gripped treatment target in the widthwise directions.

Second Embodiment

A second embodiment of the disclosed technology will be described hereinafter with reference to FIGS. 9 through 13. The second embodiment is a modification, described hereinafter, of the previous embodiment, etc. Those parts of the second embodiment that are identical to those of the previous embodiment, etc. are denoted by identical numeral references, and their description will be omitted hereinafter.

Figure 9:
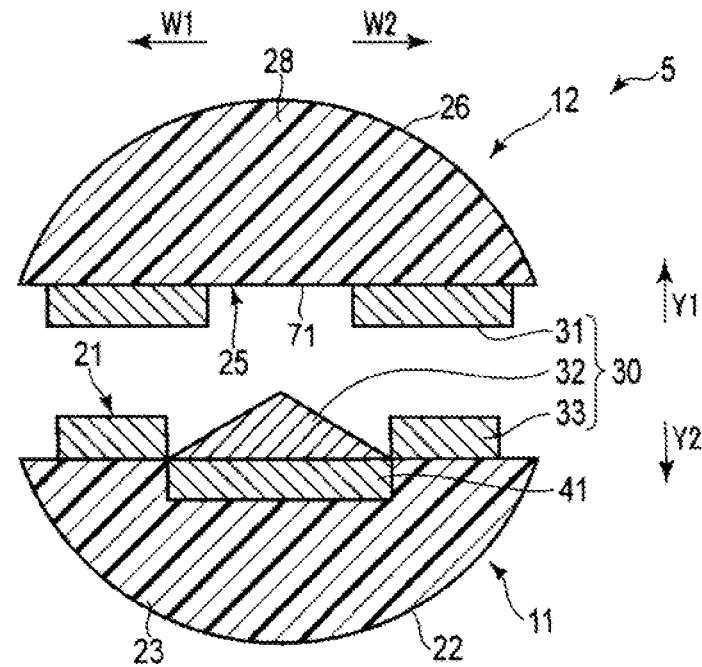
FIG. 9 is a schematic view illustrating a cross section of an end effector according to a second embodiment, taken along a plane substantially perpendicular to directions along a longitudinal axis thereof.

FIG. 9 is a view illustrating a cross section of the end effector 5, taken along a plane substantially perpendicular to directions along the longitudinal axis C. According to the present embodiment, as illustrated in FIG. 9, the first electrode 31 is disposed on the grasp 12, and the second electrode 32 and the third electrode 33 are disposed on the grasp 11. According to the present embodiment, therefore, the grasp 12 with the first electrode 31 disposed thereon is referred to as a first grasp, whereas the grasp 11 with the second electrode 32 disposed thereon is referred to as a second grasp. The second electrode 32 is disposed on the gripping surface 21 of the grasp 11 at a central portion thereof in the widthwise directions of the end effector 5. The third electrode 33 on the gripping surface 21 is disposed outwardly of the second electrode 32 in the widthwise directions of the end effector 5. The third electrode 33 is disposed on each of the both sides of the second electrode 32 in the widthwise directions of the end effector 5. The second electrode 32 and the third electrode 33 are electrically insulated from each other.

The gripping surface 25 of the grasp 12 includes a bearing surface 71 at a central portion thereof in the widthwise directions of the end effector 5. The bearing surface 71 is defined by the surface of the support body 28 and is electrically insulative. On the gripping surface 25, the first electrode 31 is disposed outwardly of the bearing surface 71 in the widthwise directions of the end effector 5. The first electrode 31 is disposed on each of the both sides of the bearing surface 71 in the widthwise directions of the end effector 5. When the space between the grasps 11 and 12 is closed, the second electrode 32 on the grasp 11 can abut against the bearing surface 71 of the grasp 12. When the second electrode 32 abuts against the bearing surface 71, the first electrode 31 is spaced from the second electrode 32 and the third electrode 33 and kept out of contact with the second electrode 32 and the third electrode 33. According to the present embodiment, therefore, in the end effector 5, the first electrode 31 is effectively prevented from contacting the second electrode 32 and the third electrode 33.

According to the present embodiment, moreover, the grasp 11 as the second grasp includes the heater 41 as the treatment energy source. The heater 41 is disposed in the grasp 11 at the central portion thereof in the widthwise directions of the end effector 5. The heater 41 is disposed on the rear surface 22 side of the second electrode 32. Heater heat generated by the heater 41 is transmitted to the second electrode 32, and is then applied from the second electrode 32 to the gripped treatment target.

According to the present embodiment, the heater 41 and the heater power supply 53 are electrically connected to each other and the bipolar electrode 30 and the high-frequency power supply 57 are electrically connected to each other in the same manner as with the first embodiment. According to the present embodiment, however, in the incising mode, the bipolar electrode 30 is supplied with high-frequency electric power in the first supply state. In the incising mode, therefore, no high-frequency electric power is supplied to the third electrode 33, but high-frequency electric power is supplied to only the first electrode 31 and the second electrode 32. According to the present embodiment, furthermore, in the sealing mode, the bipolar electrode 30 is supplied with high-frequency electric power in the second supply state. In the sealing mode, therefore, all the first through third electrodes 31 through 33 are supplied with the high-frequency electric power. When the second electrode 32 and the third electrode 33 are supplied with high-frequency electric power, the second electrode 32 and the third electrode 33 develop respective potentials that are the same as each other.

Figure 10A:
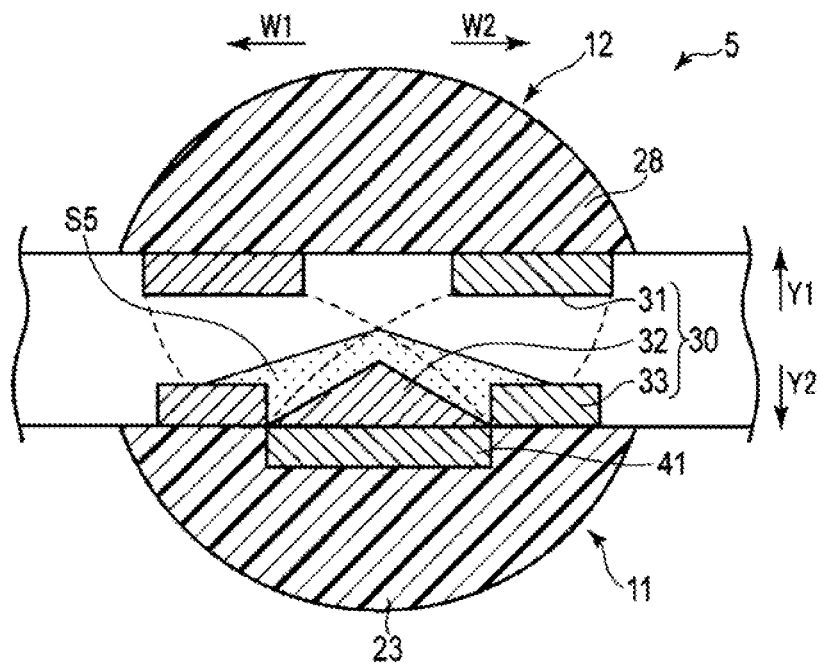
FIG. 10A is a schematic view illustrating by way of example a first temperature distribution developed in a treatment target while a power supply device according to the second embodiment is outputting power in an incising mode.
Figure 10B:
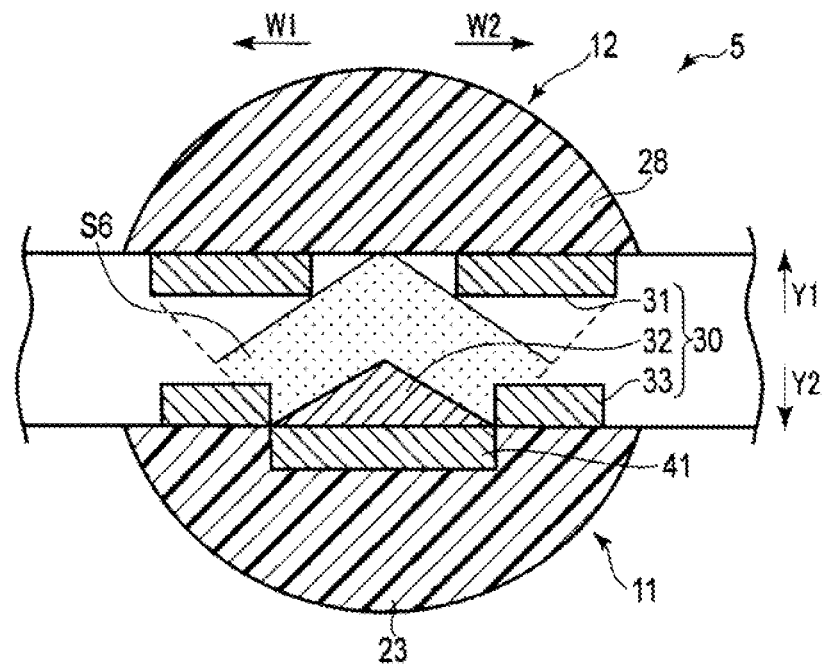
FIG. 10B is a schematic view illustrating by way of example a second temperature distribution developed in the treatment target while the power supply device according to the second embodiment is outputting power in the incising mode.
Figure 11:
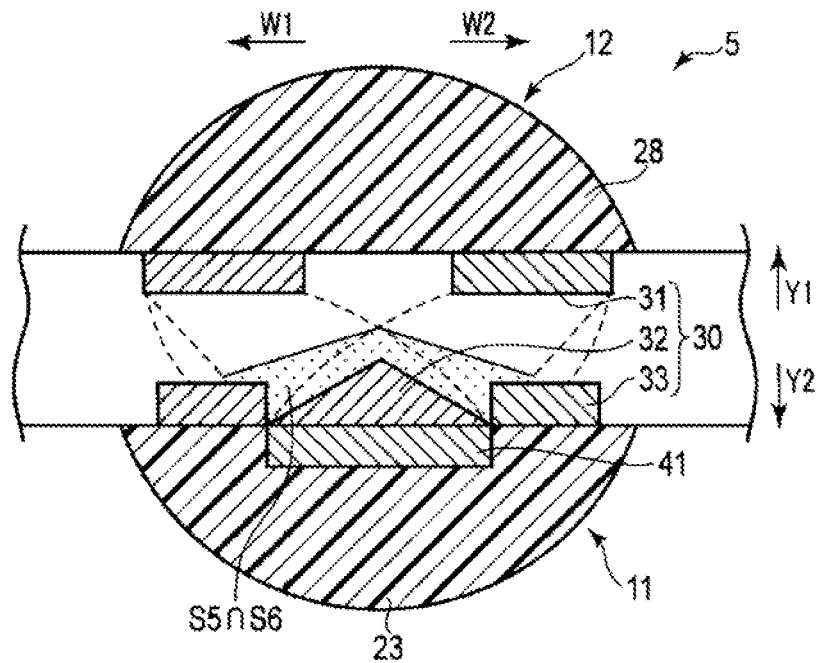
FIG. 11 is a schematic view illustrating by way of example a temperature distribution developed in the treatment target by both a high-frequency current and heater heat while the power supply device according to the second embodiment is outputting power in the incising mode.
Figure 12A:
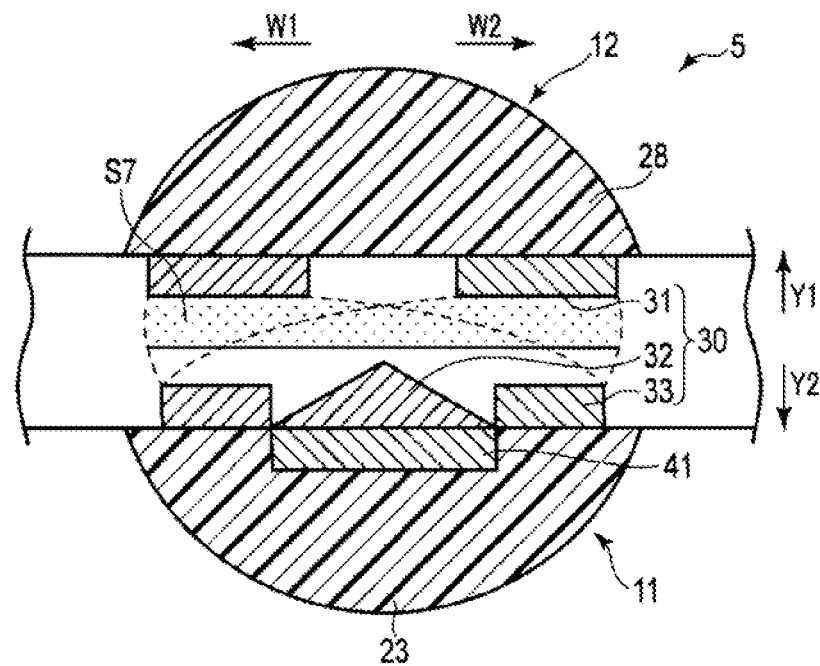
FIG. 12A is a schematic view illustrating by way of example a first temperature distribution developed in a treatment target while the power supply device according to the second embodiment is outputting power in a sealing mode.
Figure 12B:
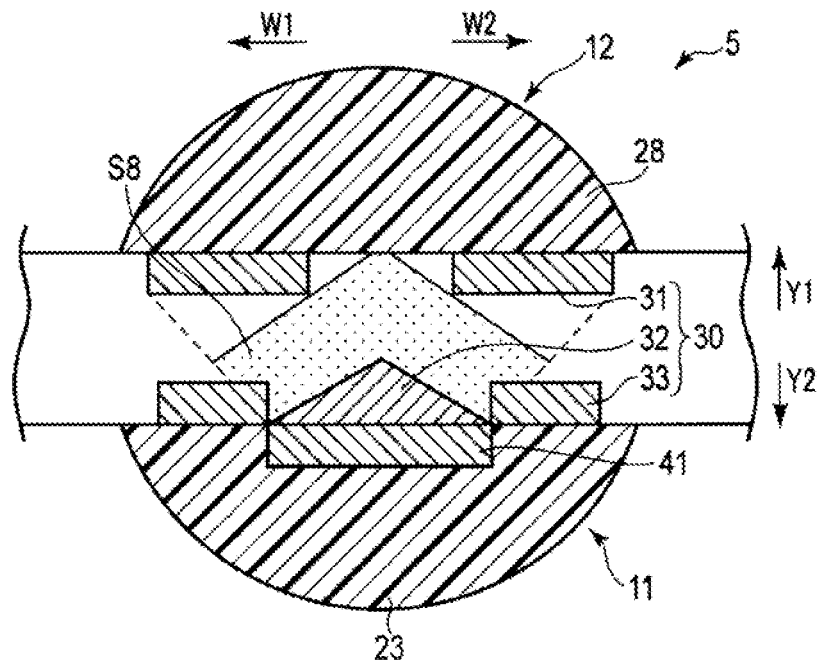
FIG. 12B is a schematic view illustrating by way of example a second temperature distribution developed in the treatment target while the power supply device according to the second embodiment is outputting power in the sealing mode.
Figure 13:
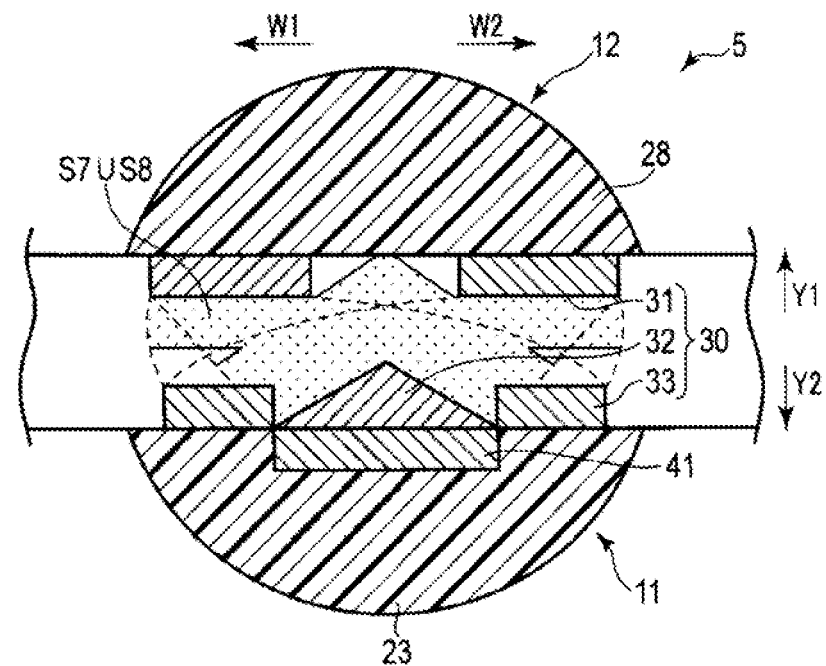
FIG. 13 is a schematic view illustrating by way of example a temperature distribution developed in the treatment target by both a high-frequency current and heater heat while the power supply device according to the second embodiment is outputting power in the sealing mode.

FIG. 10A illustrates by way of example a first temperature distribution developed in the treatment target while the power supply device 17 is outputting power in the incising mode. FIG. 10B illustrates by way of example a second temperature distribution developed in the treatment target while the power supply device 17 is outputting power in the incising mode. FIG. 11 illustrates by way of example a temperature distribution developed in the treatment target by both a high-frequency current and heater heat while the power supply device 17 is outputting power in the incising mode. The temperature distribution illustrated in FIG. 11 represents a combination of the first temperature distribution illustrated in FIG. 10A and the second temperature distribution illustrated in FIG. 10B. FIG. 12A illustrates by way of example a first temperature distribution developed in the treatment target while the power supply device 17 is outputting power in the sealing mode. FIG. 12B illustrates by way of example a second temperature distribution developed in the treatment target while the power supply device 17 is outputting power in the sealing mode. FIG. 13 illustrates by way of example a temperature distribution developed in the treatment target by both a high-frequency current and heater heat while the power supply device 17 is outputting power in the sealing mode. The temperature distribution illustrated in FIG. 13 represents a combination of the first temperature distribution illustrated in FIG. 12A and the second temperature distribution illustrated in FIG. 12B.

According to the present embodiment, in the incising mode, high-frequency electric power is supplied to only the first electrode 31 and the second electrode 32, and no high-frequency electric power is supplied to the third electrode 33. The surface area of the first electrode 31 is larger than the surface area of the second electrode 32. In the incising mode, therefore, the area of the treatment target that is relatively close to the second electrode 32, i.e., the grasp 11, is an area where the current density of the high-frequency current is relatively high, and the area of the treatment target that is relatively close to the first electrode 31, i.e., the grasp 12, is an area where the current density of the high-frequency current is relatively low. Therefore, as illustrated in FIG. 10A, according to the first temperature distribution developed in the incising mode, i.e., in the first supply state according to the present embodiment, an area S5 of the treatment target where the temperature is relatively high is positioned in an area relatively close to the second electrode 32, i.e., the grasp 11 as the second grasp, and the area of the treatment target where the temperature is relatively low is positioned in an area relatively close to the first electrode 31, i.e., the grasp 12 as the first grasp. In FIG. 10A, the area S5 where the temperature is relatively high is depicted stippled. In the area S5, the temperature goes higher toward the second electrode 32.

In the incising mode, heater heat is applied from the second electrode 32 on the grasp 11 as the second grasp to the treatment target. In the treatment target, the heater heat is transmitted from the grasp 11 side to the grasp 12 side. Therefore, as illustrated in FIG. 10B, according to the second temperature distribution developed in the incising mode, an area S6 of the treatment target where the temperature is relatively high is positioned in an area relatively close to the second electrode 32, i.e., the grasp 11 as the second grasp, and the area of the treatment target where the temperature is relatively low is positioned in an area relatively close to the grasp 12 as the first grasp. In FIG. 10B, the area S6 where the temperature is relatively high is depicted stippled. In the area S6, the temperature goes higher toward the second electrode 32.

Since the first temperature distribution and the second temperature distribution are developed as described hereinbefore in the incising mode, the area S5 where the temperature is relatively high according to the first temperature distribution is positioned in the area S6 where the temperature is relatively high according to the second temperature distribution in the incising mode, according to the present embodiment in the same manner as with the first embodiment. In the incising mode, the area where the temperature is relatively low according to the second temperature distribution is positioned in the area where the temperature is relatively low according to the first temperature distribution. In the temperature distribution illustrated in FIG. 11, the range shared by the high-temperature area S5 according to the first temperature distribution illustrated in FIG. 10A and the high-temperature area S6 according to the second temperature distribution illustrated in FIG. 10B is depicted stippled. In the incising mode, actually, as indicated by the temperature distribution in FIG. 11, only the portion of the treatment target gripped between the grasps 11 and 12 in the vicinity of the second electrode 32 is in the range shared by the high-temperature area S5 according to the first temperature distribution and the high-temperature area S6 according to the second temperature distribution. As the temperature distribution described hereinbefore is developed, the treatment target such as a blood vessel is incised quickly according to the present embodiment as with the first embodiment.

According to the present embodiment, in the sealing mode, high-frequency electric power is supplied to all the first through third electrodes 31 through 33. When the second electrode 32 and the third electrode 33 are supplied with high-frequency electric power, the second electrode 32 and the third electrode 33 develop respective potentials that are the same as each other. As described hereinbefore, the surface area of the first electrode 31 is smaller than the sum of the surface area of the second electrode 32 and the surface area of the third electrode 33. In the sealing mode, therefore, the area of the treatment target that is relatively close to the first electrode 31, i.e., the grasp 12, is an area where the current density of the high-frequency current is relatively high, and the area of the treatment target that is relatively close to the second electrode 32 and the third electrode 33, i.e., the grasp 11, is an area where the current density of the high-frequency current is relatively low. Consequently, according to the first temperature distribution developed in the sealing mode, i.e., the second supply state according to the present embodiment, as illustrated in FIG. 12A, an area S7 of the treatment target where the temperature is relatively high is positioned in an area relatively close to the first electrode 31, i.e., the grasp 12 as the first grasp, and the area of the treatment target where the temperature is relatively low is positioned in an area relatively close to the second electrode 32 and the third electrode 33, i.e., the grasp 11 as the second grasp. In FIG. 12A, the area S7 where the temperature is relatively high is depicted stippled. In the area S7, the temperature goes higher toward the first electrode 31.

As illustrated in FIG. 12B, according to the second temperature distribution developed in the sealing mode, as with the second temperature distribution developed in the incising mode, an area S8 of the treatment target where the temperature is relatively high is positioned in an area relatively close to the second electrode 32, i.e., the grasp 11 as the second grasp, and the area of the treatment target where the temperature is relatively low is positioned in an area relatively close to the grasp 12 as the first grasp. According to the present embodiment, however, the temperature of the treatment target is higher according to the second temperature distribution developed in the sealing mode than according to the second temperature distribution developed in the incising mode. In FIG. 12B, the area S8 where the temperature is relatively high is depicted stippled. In the area S8, the temperature goes higher toward the second electrode 32.

Since the first temperature distribution and the second temperature distribution are developed as described hereinbefore in the sealing mode, the area S7 where the temperature is relatively high according to the first temperature distribution is positioned in the area where the temperature is relatively low according to the second temperature distribution in the sealing mode, according to the present embodiment in the same manner as with the first embodiment. In the sealing mode, the area S8 where the temperature is relatively low according to the second temperature distribution is positioned in the area where the temperature is relatively low according to the first temperature distribution. In the temperature distribution illustrated in FIG. 13, the range covering the high-temperature area S7 according to the first temperature distribution illustrated in FIG. 12A or the high-temperature area S8 according to the second temperature distribution illustrated in FIG. 12B is depicted stippled. In the sealing mode, actually, as indicated by the temperature distribution in FIG. 13, most of the treatment target gripped between the grasps 11 and 12 is in the range covering the high-temperature area S7 according to the first temperature distribution or the high-temperature area S8 according to the second temperature distribution. As the temperature distribution described hereinbefore is developed, an uneven temperature distribution in the treatment target is restrained, resulting in an increased capability for sealing the treatment target such as a blood vessel or the like, according to the present embodiment as with the first embodiment.

Modifications of the Second Embodiment

Figure 14:
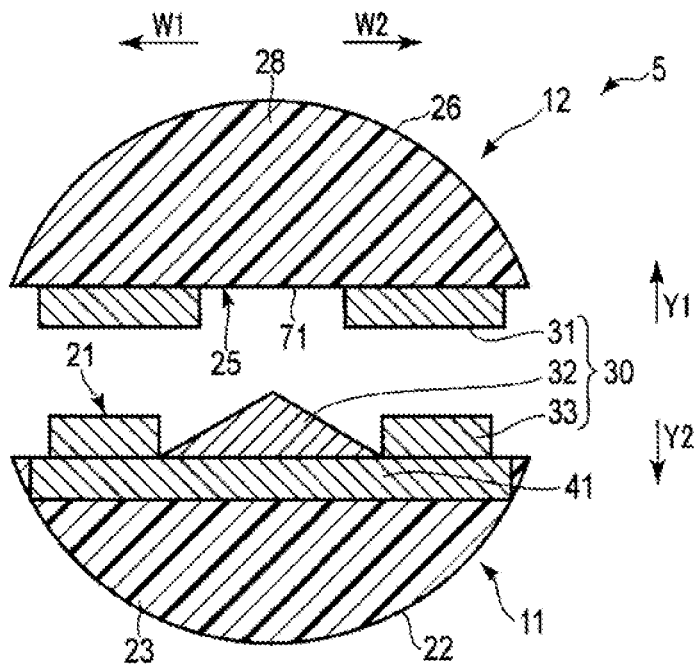
FIG. 14 is a schematic view illustrating a cross section of an end effector according to a first modification of the second embodiment, taken along a plane substantially perpendicular to directions along a longitudinal axis thereof.

According to a first modification illustrated in FIG. 14, the heater 41 extends over substantially the entire dimension of the grasp 11 as the second grasp in the widthwise directions of the end effector 5. Therefore, the heater 41 extends from a region on the rear surface 22 side of the second electrode 32 to a region on the rear surface 22 side of the third electrode 33. Heater heat generated by the heater 41 is transmitted to the third electrode 33 in addition to the second electrode 32, and applied to a treatment target gripped by both the second electrode 32 and the third electrode 33. The surface areas of the first through third electrodes 31 through 33 are related to each other in the same manner as with the second embodiment. According to the present modification, in each of the sealing mode and the incising mode, the supply of high-frequency electric power to the bipolar electrode 30 and the supply of electric energy to the heater 41 are controlled by the processor 51 in the same manner as with the second embodiment.

In the present modification, therefore, according to the first temperature distribution developed in the incising mode, the area where the temperature is relatively high is positioned in the area that is relatively close to the second electrode 32, i.e., the grasp 11 as the second grasp. According to the second temperature distribution developed in the incising mode, the area where the temperature is relatively high is positioned in the area that is relatively close to the grasp 11 as the second grasp, i.e., the area that is relatively close to the second electrode 32 and the third electrode 33 according to the present modification. According to the present modification, therefore, in the incising mode, the area where the temperature is relatively high according to the first temperature distribution is positioned in the area where the temperature is relatively high according to the second temperature distribution.

In the present modification, according to the first temperature distribution developed in the sealing mode, the area where the temperature is relatively high is positioned in the area that is relatively close to the first electrode 31, i.e., the grasp 12 as the first grasp. According to the second temperature distribution developed in the sealing mode, the area where the temperature is relatively high is positioned in the area that is relatively close to the grasp 11. According to the present modification, therefore, in the sealing mode, the area where the temperature is relatively high according to the first temperature distribution is positioned in the area where the temperature is relatively low according to the second temperature distribution.

Consequently, the present modification operates in the same manner as and offers the same advantages as with the second embodiment. According to the present modification, heater heat is applied from the second electrode 32 and the third electrode 33 to the treatment target. Therefore, the heater heat is transmitted to the treatment target over a wide area in the widthwise directions of the end effector 5. In the sealing mode, temperature unevenness is restrained from occurring in the treatment target over the wide area in the widthwise directions of the end effector 5, resulting in an increased capability for sealing the treatment target over the wide area in the widthwise directions of the end effector 5.

Figure 15:
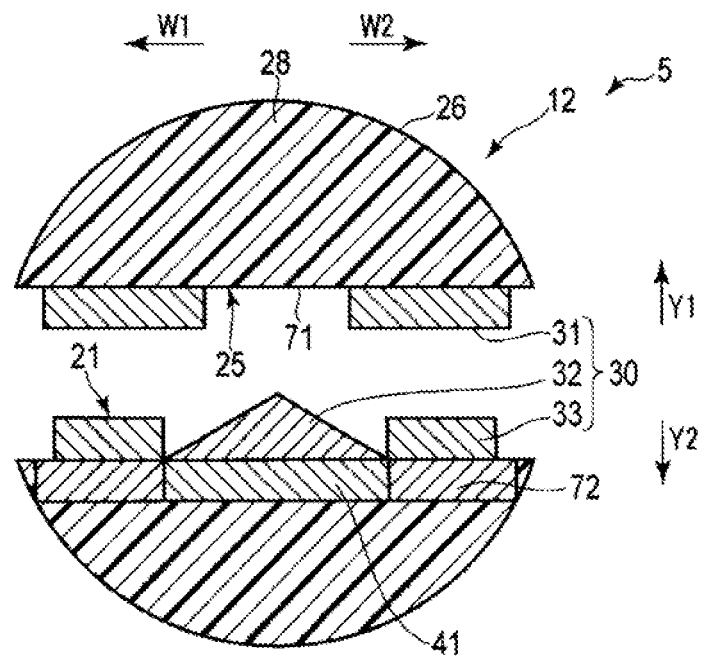
FIG. 15 is a schematic view illustrating a cross section of an end effector according to a second modification of the second embodiment, taken along a plane substantially perpendicular to directions along a longitudinal axis thereof.
Figure 16:
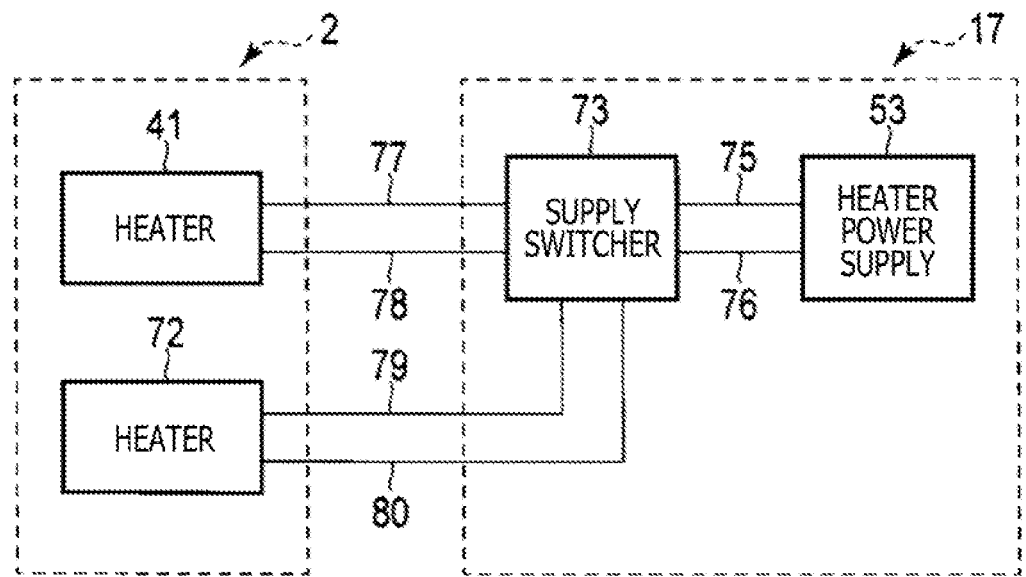
FIG. 16 is a block diagram schematically illustrating electric connections between a heater power supply and heaters according to the second modification of the second embodiment.

According to a second modification illustrated in FIGS. 15 and 16, a heater, i.e., second heater 72 is disposed outwardly of the heater, i.e., first heater 41 in the widthwise directions of the end effector 5. The heater 72 is disposed on each of the both sides of the heater 41 in the widthwise directions of the end effector 5. The heater 72 is disposed on the rear surface 22 side of the third electrode 33. Heater heat generated by the heater 72 is transmitted to the third electrode 33, and is then applied from the third electrode 33 to the gripped treatment target. According to the present modification, heater heat generated by the heater 41 is transmitted to the second electrode 32, and is then applied from the second electrode 32 to the gripped treatment target. The surface areas of the first through third electrodes 31 through 33 according to the present modification are related to each other in the same manner as with the second embodiment. According to the present modification, in each of the sealing mode and the incising mode, the supply of high-frequency electric power to the bipolar electrode 30 is controlled by the processor 51 in the same manner as with the second embodiment.

FIG. 16 illustrates electric connections between the heater power supply 53 and the heaters 41 and 72 as treatment energy sources according to the present modification. According to the present modification, the power supply device 17 includes a supply switcher 73 in the form of a switch circuit or the like, separately from the supply switcher 61. The supply switcher 73 is electrically connected to the heater power supply 53 through electric lines 75 and 76 in the power supply device 17. The supply switcher 73 is also electrically connected to the heater, i.e., first heater 41 through electric lines 77 and 78 and is also electrically connected to the heater, i.e., second heater 72 through electric lines 79 and 80. Each of the electric lines 77 through 80 extends through the cable 15, the housing 4, and the shaft 3. The processor 51 controls operation of the supply switcher 73.

According to the present modification, the processor 51 controls the output from the heater power supply 53 and operation of the supply switcher 73 to control the supply of electric energy to the heaters 41 and 72. When the processor 51 controls operation of the supply switcher 73, the supply of electric energy to the heaters 41 and 72 is switched between the first supply state and the second supply state. When the supply of electric energy to the heaters 41 and 72 switched between the first supply state and the second supply state, the state in which heater heat is applied to the treatment target varies. According to the present modification, electric energy is supplied to the heaters 41 and 72 in the first supply state in the incising mode, and electric energy is supplied to the heaters 41 and 72 in the second supply state in the sealing mode.

In the first supply state, the supply switcher 73 interrupts electric connections of the electric lines 79 and 80 to the electric lines 75 and 76. In the first supply state, therefore, no electric energy is supplied to the heater, i.e., the second heater 72, and the heater 72 does not generate heater heat. At this time, the heater power supply 53 supplies heater electric power through the electric lines 75 through 78 to the heater, i.e., the first heater 41, causing the heater 41 to generate heater heat. In the first supply state, consequently, only the heater heat generated by the heater 41 is applied to the treatment target, and the heater heat is applied mainly from the second electrode 32 to the treatment target.

In the second supply state, the supply switcher 73 electrically connects the electric lines 79 and 80 to the electric lines 75 and 76. In the second supply state, therefore, electric energy is supplied to the heater 72, and the heater 72 generates heater heat. In the second supply state, heater electric power is supplied from the heater power supply 53 to the heater 41, and the heater 41 generates heater heat. In the second supply state, therefore, both the heater heat generated by the heater 41 and the heater heat generated by the heater 72 are applied to the treatment target. The heater heat is applied from both the second electrode 32 and the third electrode 33 to the treatment target.

In the present modification, according to the first temperature distribution developed in the incising mode, the area where the temperature is relatively high is positioned in the area that is relatively close to the second electrode 32, i.e., the grasp 11 as the second grasp. According to the second temperature distribution developed in the incising mode, the area where the temperature is relatively high is positioned in the area that is relatively close to the grasp 11 as the second grasp, i.e., the area that is relatively close to the second electrode 32 according to the present modification. According to the present modification, therefore, in the incising mode, the area where the temperature is relatively high according to the first temperature distribution is positioned in the area where the temperature is relatively high according to the second temperature distribution. According to the present modification, the treatment target such as a blood vessel or the like is incised quickly as with the second embodiment.

According to the present modification, in the incising mode, electric energy is supplied to the heaters 41 and 72 in the first supply state, and only the heater 41 generates heater heat. In the incising mode, therefore, the heater heat is applied to the treatment target from the second electrode 32 that is positioned mainly at a central portion of the gripping surface 21 in the widthwise directions. In the incising mode, the heater heat is applied from the second electrode 32 intensively to the area where the temperature is relatively high according to the first temperature distribution due to the high-frequency current. Accordingly, the treatment target is incised more quickly.

In the present modification, according to the first temperature distribution developed in the sealing mode, the area where the temperature is relatively high is positioned in the area that is relatively close to the first electrode 31, i.e., the grasp 12 as the first grasp. According to the second temperature distribution developed in the sealing mode, the area where the temperature is relatively high is positioned in the area that is relatively close to the grasp 11. According to the present modification, therefore, in the sealing mode, the area where the temperature is relatively high according to the first temperature distribution is positioned in the area where the temperature is relatively low according to the second temperature distribution. According to the present modification, therefore, as with the second embodiment, temperature unevenness is restrained from occurring in the treatment target, resulting in an increased capability for sealing the treatment target such as a blood vessel or the like.

According to the present modification, in the sealing mode, electric energy is supplied to the heaters 41 and 72 in the second supply state, and both the heater 41 and the heater 72 generate heater heat. In the sealing mode, therefore, the heater heat is applied to the treatment target from both the second electrode 32 and the third electrode 33 on the gripping surface 21. Therefore, the heater heat is transmitted to the treatment target over a wide area in the widthwise directions of the end effector 5. In the sealing mode, therefore, temperature unevenness is restrained from occurring in the treatment target over the wide area in the widthwise directions of the end effector 5, resulting in an increased capability for sealing the treatment target over the wide area in the widthwise directions of the end effector 5.

Common Matters of the First Embodiment, the Second Embodiment, and the Modifications of These Embodiments According to the first embodiment, the second embodiment, and the modifications of these embodiments, the processor 51 is capable of switching the supply of high-frequency electric power to the bipolar electrode 30 between the two supply states, i.e., the first supply state and the second supply state. The area where the temperature is relatively high according to the first temperature distribution developed in one of the supply states is positioned in the area where the temperature is relatively low according to the second temperature distribution. The area where the temperature is relatively high according to the first temperature distribution developed in the other of the supply states is positioned in the area where the temperature is relatively high according to the second temperature distribution.

Third Embodiment

Next, a third embodiment of the disclosed technology will be described hereinafter with reference to FIGS. 17 through 22. The third embodiment is a modification, described hereinafter, of the arrangements of the previous embodiments, etc. Those parts of the third embodiment that are identical to those of the previous embodiments, etc. are denoted by identical numeral references, and their description will be omitted hereinafter.

Figure 17:
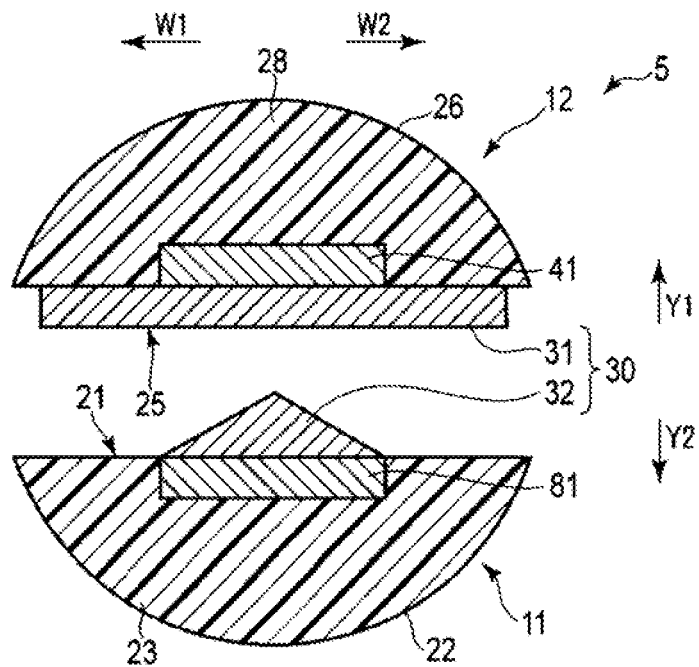
FIG. 17 is a schematic view illustrating a cross section of an end effector according to a third embodiment, taken along a plane substantially perpendicular to directions along a longitudinal axis thereof.

FIG. 17 is a view illustrating a cross section of the end effector 5, taken along a plane substantially perpendicular to directions along the longitudinal axis C. According to the present embodiment, as illustrated in FIG. 17, the first electrode 31 is disposed on the grasp 12, and the second electrode 32 is disposed on the grasp 11. According to the present embodiment, the end effector 5, i.e., the bipolar electrode 30, is free of the third electrode 33. According to the present embodiment, the grasp 12 with the first electrode 31 disposed thereon is referred to as a first grasp, whereas the grasp 11 with the second electrode 32 disposed thereon is referred to as a second grasp. According to the present embodiment, furthermore, the surface area of the first electrode 31 is larger than the surface area of the second electrode 32. The surface of at least one of the electrodes 31 and 32 includes a protrusion, not illustrated, and made of an electrically insulative material. The protrusion effectively prevents the first electrode 31 from contacting the second electrode 32.

According to the present embodiment, the heater 41 as a treatment energy source is disposed in the grasp 12 as the first grasp. The heater, i.e., first heater 41 is disposed in the grasp 12 on a rear surface 26 side of the first electrode 31. Heater heat generated by the heater 41 is transmitted to the first electrode 31, and applied from the first electrode 31 to a gripped treatment target. According to the present embodiment, moreover, a heater 81 as another treatment energy source different from the heater 41 is disposed in the grasp 11 as the second grasp. The heater, i.e., second heater 81 is disposed in the grasp 11 on the rear surface 22 side of the second electrode 32. Heater heat generated by the heater 81 is transmitted to the second electrode 32, and applied from the second electrode 32 to the gripped treatment target.

Figure 18:
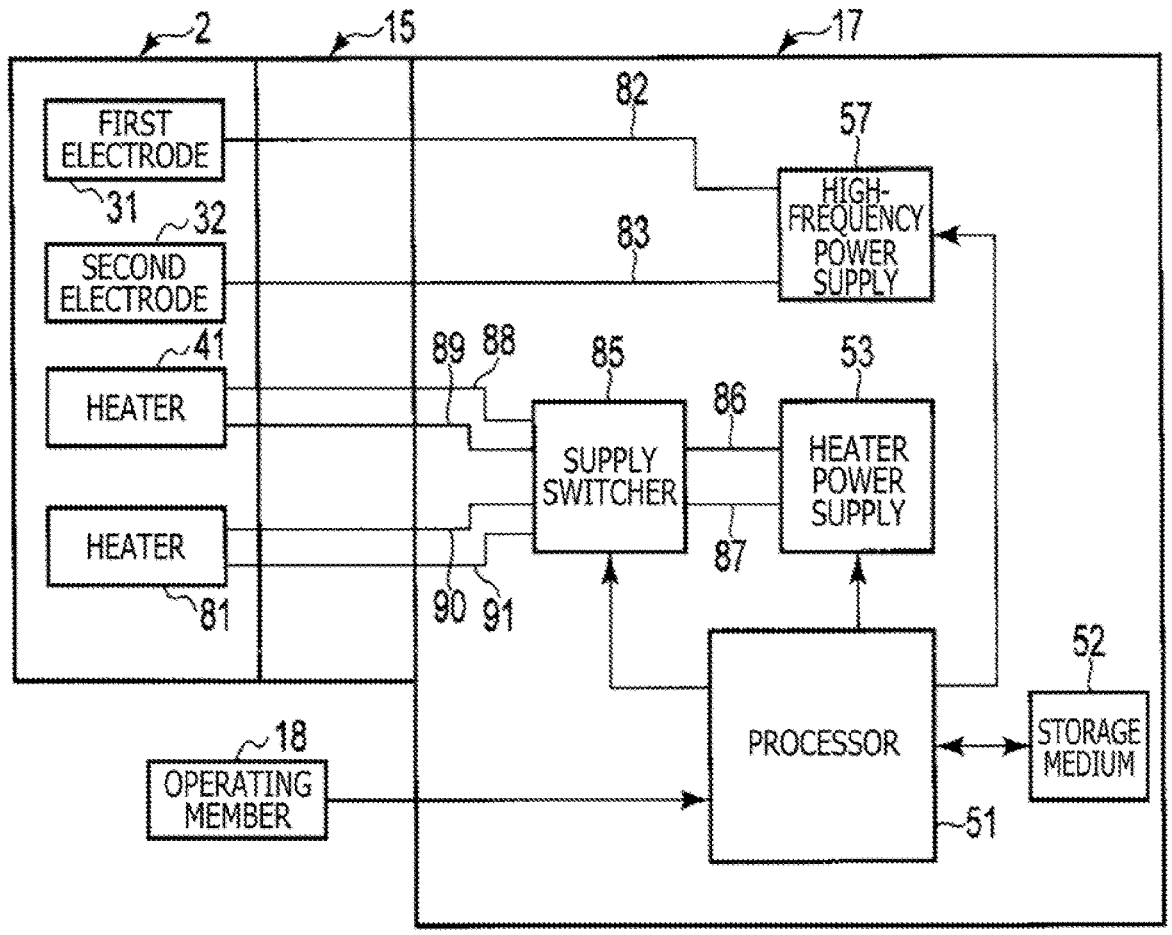
FIG. 18 is a block diagram schematically illustrating an arrangement for controlling the supply of high-frequency electric power to a bipolar electrode and the supply of electric energy to a heater according to the third embodiment.

FIG. 18 is a view is a diagram illustrating an arrangement for controlling the supply of high-frequency electric power to the bipolar electrode 30 and the supply of electric energy to the heater 41 according to the present embodiment. According to the present embodiment, as illustrated in FIG. 18, the high-frequency power supply 57 is electrically connected to the first electrode 31 through an electric line 82 and electrically connected to the second electrode 32 through an electric line 83. Each of the electric lines 82 and 83 extends through the cable 15, the housing 4, and the shaft 3. High-frequency electric power output from the high-frequency power supply 57 is supplied to the first electrode 31 through the electric line 82 and is also supplied to the second electrode 32 through the electric line 83. The first electrode 31 and the second electrode 32 develop respective potentials that are different from each other, causing a high-frequency current to flow through the treatment target gripped between the first electrode 31 and the second electrode 32.

According to the present embodiment, furthermore, the power supply device 17 includes a supply switcher 85 in the form of a switch circuit or the like, instead of the supply switcher 61. The supply switcher 85 is electrically connected to the heater power supply 53 through electric lines 86 and 87 in the power supply device 17. The supply switcher 85 is also electrically connected to the heater, i.e., first heater 41 through electric lines 88 and 89 and is also electrically connected to the heater, i.e., second heater 81 through electric lines 90 and 91. Each of the electric lines 88 through 91 extends through the cable 15, the housing 4, and the shaft 3. The processor 51 controls operation of the supply switcher 85.

According to the present embodiment, the processor 51 controls the output from the heater power supply 53 and operation of the supply switcher 85, thereby controlling the supply of electric energy to the heaters 41 and 81. When the processor 51 controls operation of the supply switcher 85, the supply of electric energy to the heaters 41 and 81 is switched between the first supply state and the second supply state. When the supply of electric energy to the heaters 41 and 81 is switched between the first supply state and the second supply state, the state in which heater heat is applied to the treatment target varies. According to the present modification, electric energy is supplied to the heaters 41 and 81 in the first supply state in the sealing mode, and electric energy is supplied to the heaters 41 and 81 in the second supply state in the incising mode.

In the first supply state, the supply switcher 85 electrically connects the electric lines 88 and 89 to the electric lines 86 and 87, and interrupts electric connections of the electric lines 90 and 91 to the electric lines 86 and 87. In the first supply state, therefore, electric energy is supplied to only the heater, i.e., first heater 41, and no electric energy is supplied to the heater, i.e., second heater 81. In the first supply state, therefore, only the heater 41 generates heater heat, and the heater 81 generates no heater heat. Since only the heater 41 generates heater heat, the heater heat is applied from the first electrode 31, i.e., the grasp 12 as the first grasp, to the treatment target in the first supply state.

In the second supply state, the supply switcher 85 electrically connects the electric lines 90 and 91 to the electric lines 86 and 87, and interrupts electric connections of the electric lines 88 and 89 to the electric lines 86 and 87. In the second supply state, therefore, electric energy is supplied to only the heater, i.e., second heater 81, and no electric energy is supplied to the heater, i.e., first heater 41. In the second supply state, therefore, only the heater 81 generates heater heat, and the heater 41 generates no heater heat. Since only the heater 81 generates heater heat, the heater heat is applied from the second electrode 32, i.e., the grasp 11 as the second grasp, to the treatment target in the second supply state.

Figure 19A:
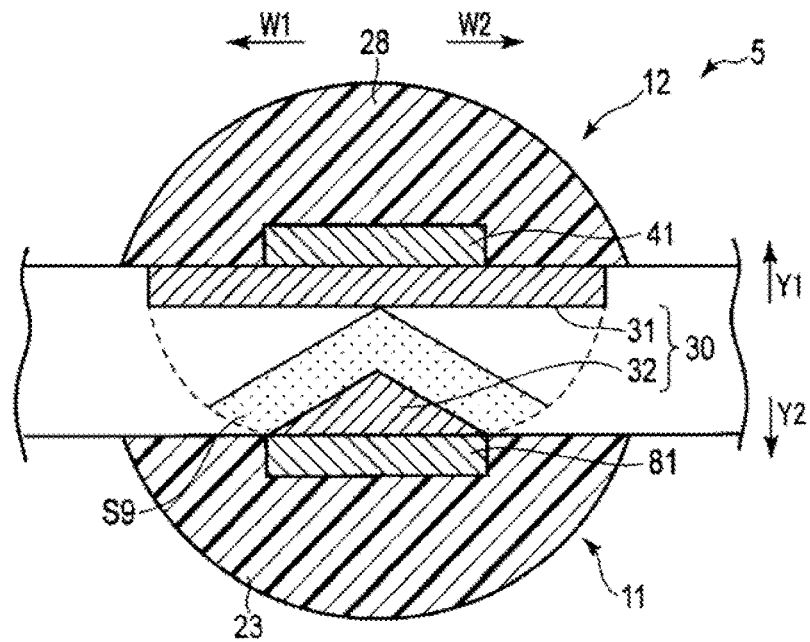
FIG. 19A is a schematic view illustrating by way of example a first temperature distribution developed in a treatment target while a power supply device according to the third embodiment is outputting power in a sealing mode.
Figure 19B:
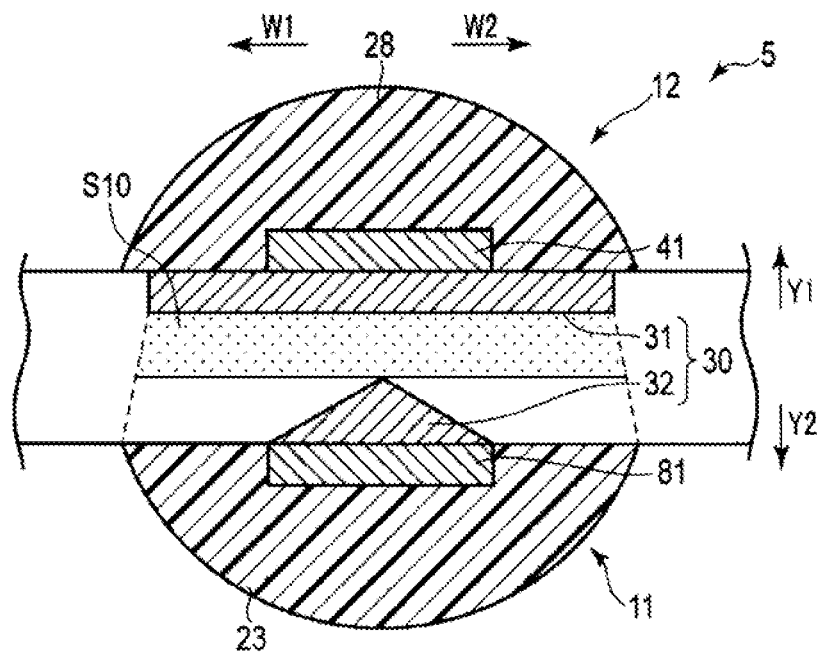
FIG. 19B is a schematic view illustrating by way of example a second temperature distribution developed in the treatment target while the power supply device according to the third embodiment is outputting power in the sealing mode.
Figure 20:
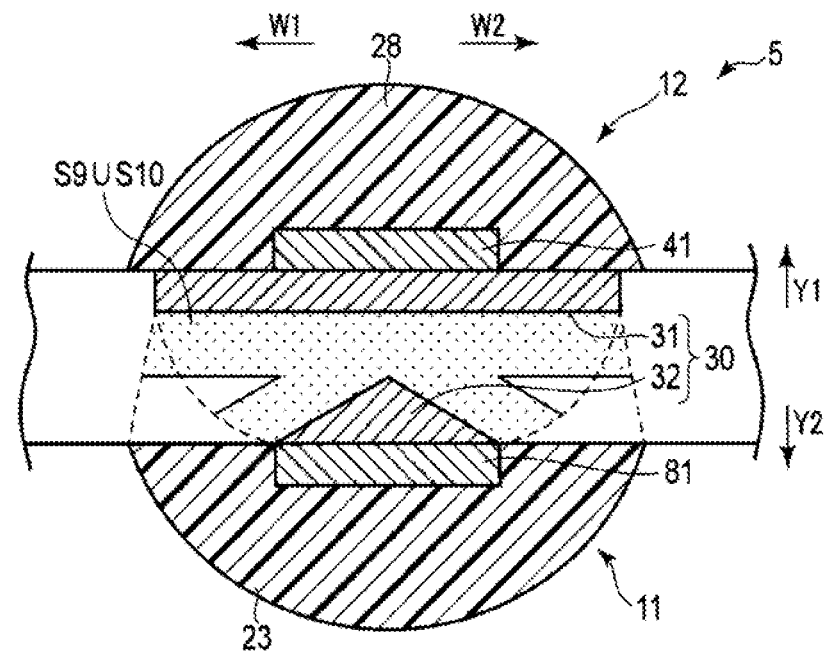
FIG. 20 is a schematic view illustrating by way of example a temperature distribution developed in the treatment target by both a high-frequency current and heater heat while the power supply device according to the third embodiment is outputting power in the sealing mode.
Figure 21A:
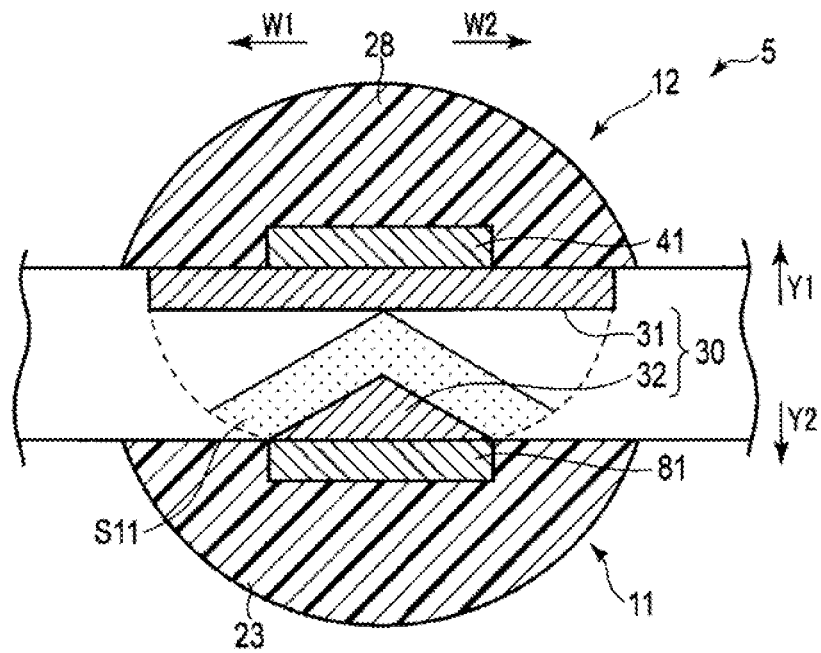
FIG. 21A is a schematic view illustrating by way of example a first temperature distribution developed in a treatment target while the power supply device according to the third embodiment is outputting power in an incising mode.
Figure 21B:
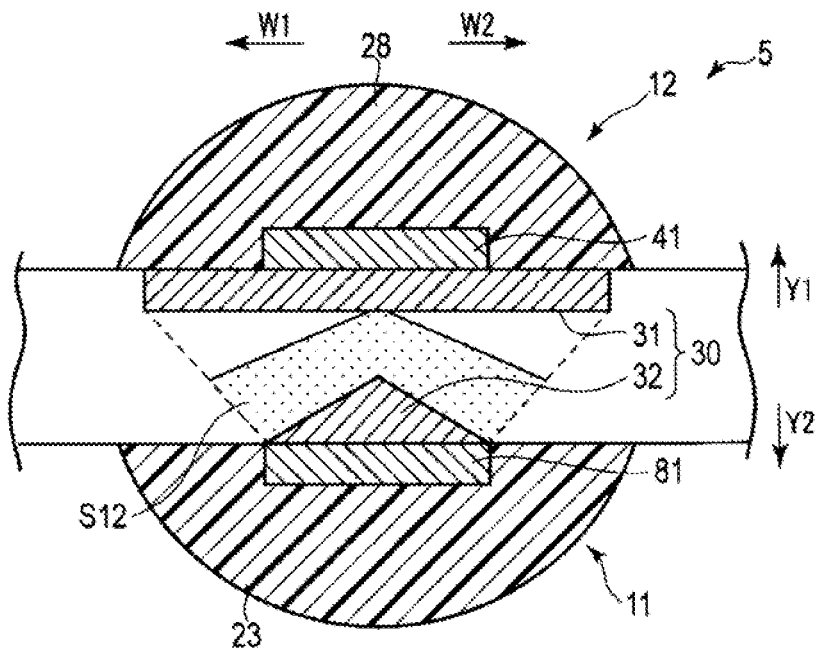
FIG. 21B is a schematic view illustrating by way of example a second temperature distribution developed in the treatment target while the power supply device according to the third embodiment is outputting power in the incising mode.
Figure 22:
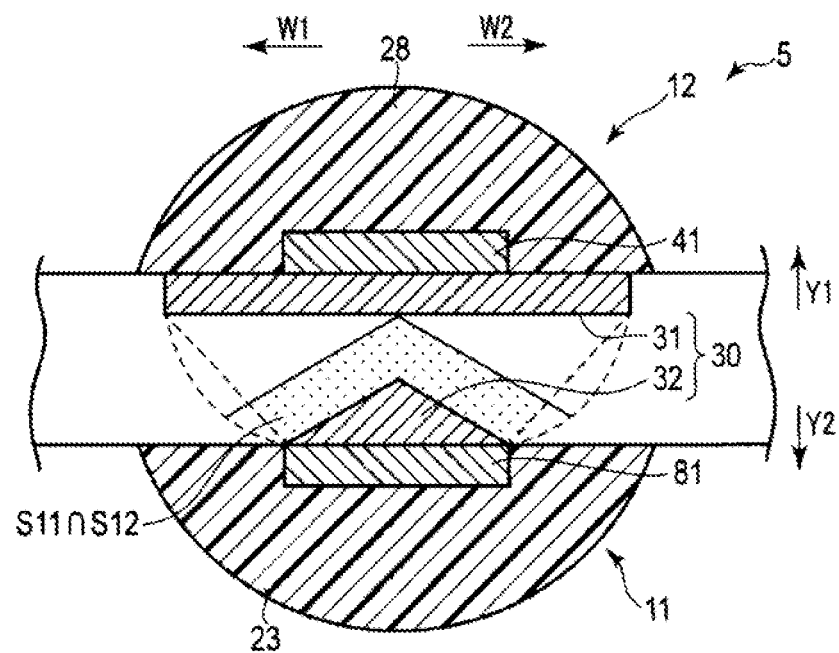
FIG. 22 is a schematic view illustrating by way of example a temperature distribution developed in the treatment target by both a high-frequency current and heater heat while the power supply device according to the third embodiment is outputting power in the incising mode.

FIG. 19A illustrates by way of example a first temperature distribution developed in the treatment target while the power supply device 17 is outputting power in the sealing mode. FIG. 19B illustrates by way of example a second temperature distribution developed in the treatment target while the power supply device 17 is outputting power in the sealing mode. FIG. 20 illustrates by way of example a temperature distribution developed in the treatment target by both a high-frequency current and heater heat while the power supply device 17 is outputting power in the sealing mode. The temperature distribution illustrated in FIG. 20 represents a combination of the first temperature distribution illustrated in FIG. 19A and the second temperature distribution illustrated in FIG. 19B. FIG. 21A illustrates by way of example a first temperature distribution developed in the treatment target while the power supply device 17 is outputting power in the incising mode. FIG. 21B illustrates by way of example a second temperature distribution developed in the treatment target while the power supply device 17 is outputting power in the incising mode. FIG. 22 illustrates by way of example a temperature distribution developed in the treatment target by both a high-frequency current and heater heat while the power supply device 17 is outputting power in the incising mode. The temperature distribution illustrated in FIG. 22 represents a combination of the first temperature distribution illustrated in FIG. 21A and the second temperature distribution illustrated in FIG. 21B.

According to the present embodiment, the surface area of the first electrode 31 is larger than the surface area of the second electrode 32. In the sealing mode, therefore, the area of the treatment target that is relatively close to the second electrode 32, i.e., the grasp 11, is an area where the current density of the high-frequency current is relatively high, and the area of the treatment target that is relatively close to the first electrode 31, i.e., the grasp 12, is an area where the current density of the high-frequency current is relatively low. Therefore, as illustrated in FIG. 19A, according to the first temperature distribution developed in the sealing mode, an area S9 of the treatment target where the temperature is relatively high is positioned in an area relatively close to the second electrode 32, i.e., the grasp 11 as the second grasp, and the area of the treatment target where the temperature is relatively low is positioned in an area relatively close to the first electrode 31, i.e., the grasp 12 as the first grasp. In FIG. 19A, the area S9 where the temperature is relatively high is depicted stippled. In the area S9, the temperature goes higher toward the second electrode 32.

In the sealing mode, only the heater 41 generates heater heat, and the heater heat is applied from the first electrode 31 on the grasp 12 as the first grasp to the treatment target. In the treatment target, the heater heat is transmitted from the grasp 12 side to the grasp 11 side. Therefore, as illustrated in FIG. 19B, according to the second temperature distribution developed in the sealing mode, an area S10 of the treatment target where the temperature is relatively high is positioned in an area relatively close to the first electrode 31, i.e., the grasp 12 as the first grasp, and the area of the treatment target where the temperature is relatively low is positioned in an area relatively close to the grasp 11 as the second grasp. In FIG. 19B, the area S10 where the temperature is relatively high is depicted stippled. In the area S10, the temperature goes higher toward the first electrode 31.

Since the first temperature distribution and the second temperature distribution are developed as described hereinbefore in the sealing mode, the area S9 where the temperature is relatively high according to the first temperature distribution is positioned in the area where the temperature is relatively low according to the second temperature distribution in the sealing mode, according to the present embodiment in the same manner as with the first embodiment. In the sealing mode, the area S10 where the temperature is relatively high according to the second temperature distribution is positioned in the area where the temperature is relatively low according to the first temperature distribution. In the temperature distribution illustrated in FIG. 20, the range covering the high-temperature area S9 according to the first temperature distribution illustrated in FIG. 19A or the high-temperature area S10 according to the second temperature distribution illustrated in FIG. 19B is depicted stippled. In the sealing mode, actually, as indicated by the temperature distribution in FIG. 20, most of the treatment target gripped between the grasps 11 and 12 is in the range covering the high-temperature area S9 according to the first temperature distribution or the high-temperature area S10 according to the second temperature distribution. As the temperature distributions described hereinbefore are developed, temperature unevenness in the treatment target is restrained, resulting in an increased capability for sealing the treatment target such as a blood vessel or the like according to the present embodiment as with the first embodiment.

As illustrated in FIG. 21A, according to the first temperature distribution developed in the incising mode, as with the first temperature distribution developed in the sealing mode, an area S11 of the treatment target where the temperature is relatively high is positioned in an area relatively close to the second electrode 32, i.e., the grasp 11 as the second grasp, and the area of the treatment target where the temperature is relatively low is positioned in an area relatively close to the grasp 12 as the first grasp. In the incising mode, however, high-frequency electric power may be output from the high-frequency power supply 57 in a state different from the sealing mode. In such a case, the temperature of the treatment target according to the second temperature distribution developed in the incising mode is different from the temperature of the treatment target according to the second temperature distribution developed in the sealing mode. In FIG. 21A, the area S11 where the temperature is relatively high is depicted stippled. In the area S11, the temperature goes higher toward the second electrode 32.

In the incising mode, only the heater 81 generates heater heat, and the heater heat is applied from the second electrode 32 on the grasp 11 as the second grasp to the treatment target. In the treatment target, the heater heat is transmitted from the grasp 11 side to the grasp 12 side. Therefore, as illustrated in FIG. 21B, according to the second temperature distribution developed in the incising mode, an area S12 of the treatment target where the temperature is relatively high is positioned in an area relatively close to the second electrode 32, i.e., the grasp 11 as the second grasp, and the area of the treatment target where the temperature is relatively low is positioned in an area relatively close to the grasp 12 as the first grasp. In the incising mode, i.e., the second supply state, the output from the heater power supply 53 should preferably higher than in the sealing mode, i.e., the first supply state. In such a case, the temperature of the heater 81 in the incising mode is higher than the temperature of the heater 41 in the sealing mode. Therefore, the temperature of the treatment target is higher according to the second temperature distribution developed in the incising mode than according to the second temperature distribution developed in the sealing mode. In FIG. 21B, the area S12 where the temperature is relatively high is depicted stippled. In the area S12, the temperature goes higher toward the second electrode 32.

Since the first temperature distribution and the second temperature distribution are developed as described hereinbefore in the incising mode, the area S11 where the temperature is relatively high according to the first temperature distribution is positioned in the area S12 where the temperature is relatively high according to the second temperature distribution in the incising mode. In the incising mode, the area where the temperature is relatively low according to the second temperature distribution is positioned in the area where the temperature is relatively low according to the first temperature distribution. In the temperature distribution illustrated in FIG. 22, the range shared by the high-temperature area S11 according to the first temperature distribution illustrated in FIG. 21A and the high-temperature area S12 according to the second temperature distribution illustrated in FIG. 21B is depicted stippled. In the incising mode, actually, as indicated by the temperature distribution in FIG. 22, only the portion of the treatment target gripped between the grasps 11 and 12 in the vicinity of the second electrode 32 is in the range shared by the high-temperature area S11 according to the first temperature distribution and the high-temperature area S12 according to the second temperature distribution. As the temperature distribution described hereinbefore is developed, the treatment target such as a blood vessel is incised quickly according to the present embodiment, as with the first embodiment.

According to the third embodiment, the processor 51 is capable of switching the supply of electric energy to the heaters 41 and 81 as the treatment energy sources between the two supply states, i.e., the first supply state and the second supply state. The area where the temperature is relatively high according to the second temperature distribution developed in one of the supply states is positioned in the area where the temperature is relatively low according to the first temperature distribution. The area where the temperature is relatively high according to the second temperature distribution developed in the other of the supply states is positioned in the area where the temperature is relatively high according to the first temperature distribution.

Fourth Embodiment

Next, a fourth embodiment of the disclosed technology will be described hereinafter with reference to FIGS. 23 through 25. The fourth embodiment is a modification, described hereinafter, of the arrangement of the first embodiment. Those parts of the fourth embodiment that are identical to those of the first embodiment are denoted by identical numeral references, and their description will be omitted hereinafter.

Figure 23:
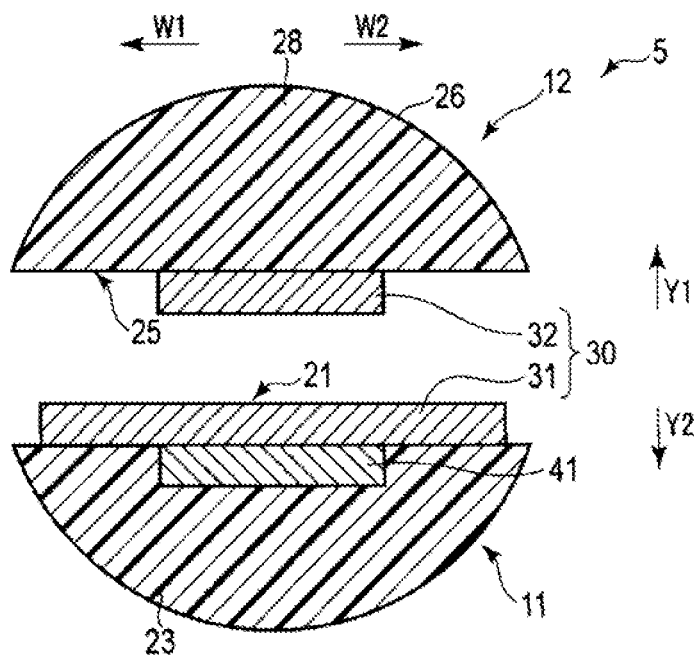
FIG. 23 is a schematic view illustrating a cross section of an end effector according to a fourth embodiment, taken along a plane substantially perpendicular to directions along a longitudinal axis thereof.

FIG. 23 is a view illustrating a cross section of the end effector 5, taken along a plane substantially perpendicular to directions along the longitudinal axis C. According to the present embodiment, as illustrated in FIG. 23, the first electrode 31 is disposed on the grasp 11, and the second electrode 32 is disposed on the grasp 12. According to the present embodiment, the grasp 11 with the first electrode 31 disposed thereon is referred to as a first grasp, whereas the grasp 12 with the second electrode 32 disposed thereon is referred to as a second grasp. According to the present embodiment, the surface area of the first electrode 31 is larger than the surface area of the second electrode 32. According to the present embodiment, furthermore, as with the third embodiment, the surface of at least one of the electrodes 31 and 32 includes a protrusion, not illustrated, made of an electrically insulative material. According to the present embodiment, when the first electrode 31 and the second electrode 32 are supplied with high-frequency electric power from the high-frequency power supply 57, the first electrode 31 and the second electrode 32 develop respective potentials that are different from each other, causing a high-frequency current to flow through the treatment target gripped between the first electrode 31 and the second electrode 32.

According to the present embodiment, the heater 41 as the treatment energy source is disposed in the grasp 11 as the first grasp. The heater 41 is disposed on the rear surface 22 side of the first electrode 31. When the heater 41 is supplied with electric energy from the heater power supply 53, the heater 41 generates heater heat. The heater heat generated by the heater 41 is transmitted to the first electrode 31, and is then applied from the first electrode 31 to the gripped treatment target.

Figure 24A:
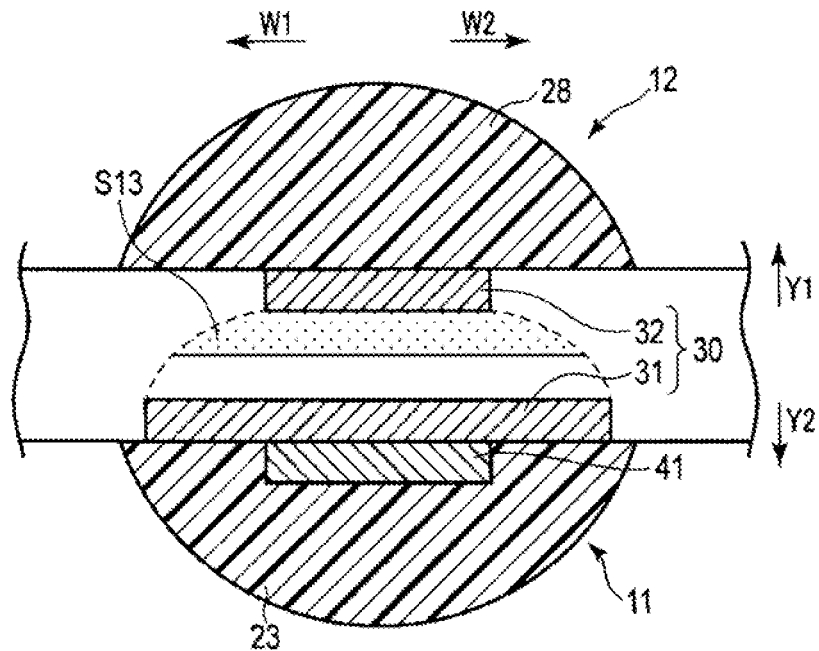
FIG. 24A is a schematic view illustrating by way of example a first temperature distribution developed in a treatment target by a high-frequency current flowing between electrodes according to the fourth embodiment.
Figure 24B:
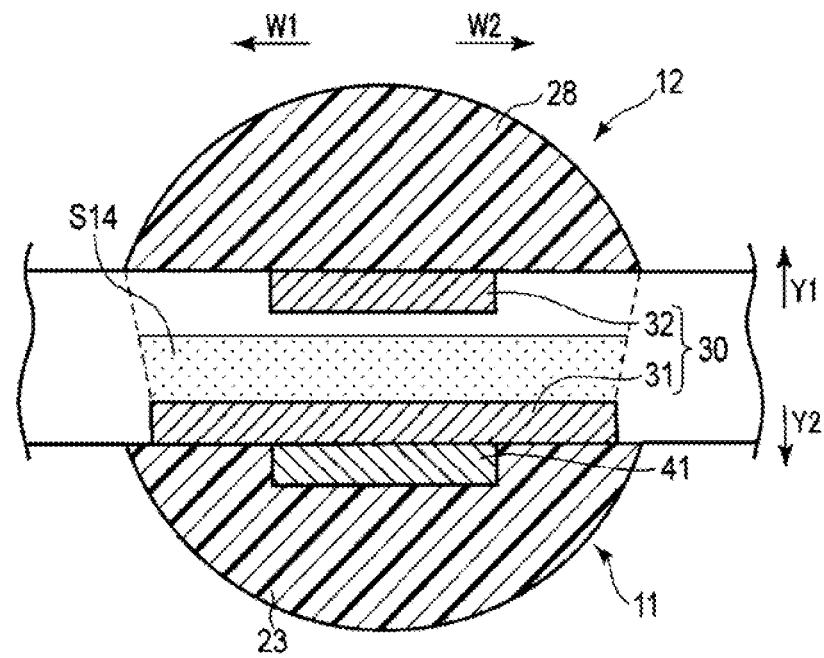
FIG. 24B is a schematic view illustrating by way of example a second temperature distribution developed in the treatment target by heater heat generated by a heater according to the fourth embodiment.
Figure 25:
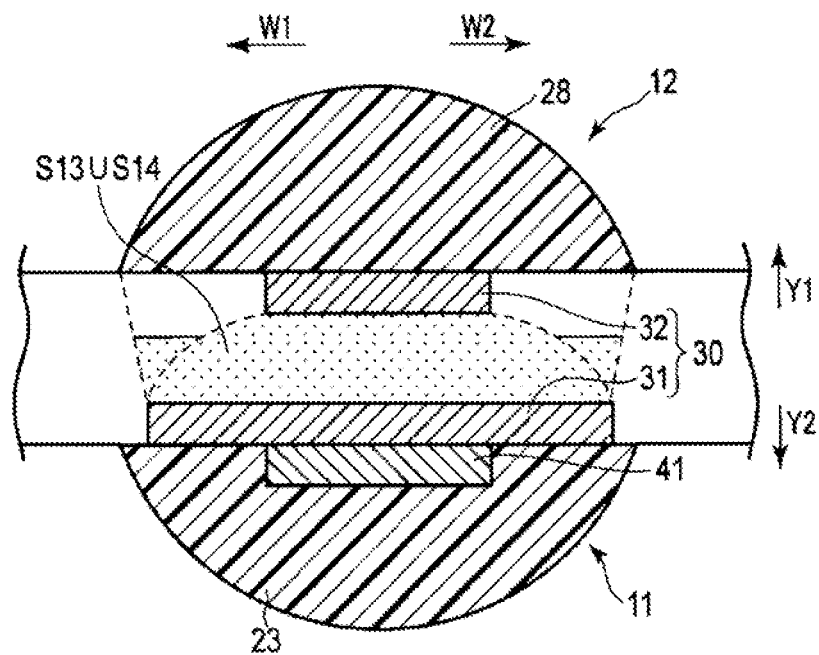
FIG. 25 is a schematic view illustrating by way of example a temperature distribution developed in the treatment target by both the high-frequency current and the heater heat while the power supply device according to the fourth embodiment is outputting power.

FIG. 24A illustrates by way of example a first temperature distribution developed in the treatment target due to a high-frequency current flowing between the electrodes 31 and 32. FIG. 24B illustrates by way of example a second temperature distribution developed in the treatment target due to heater heat generated by the heater 41. FIG. 25 illustrates by way of example a temperature distribution developed in the treatment target by both a high-frequency current and heater heat while the power supply device 17 is outputting power in the sealing mode. The temperature distribution illustrated in FIG. 25 represents a combination of the first temperature distribution illustrated in FIG. 24A and the second temperature distribution illustrated in FIG. 24B.

According to the present embodiment, the surface area of the first electrode 31 is larger than the surface area of the second electrode 32. Therefore, the area of the treatment target that is relatively close to the second electrode 32, i.e., the grasp 12, is an area where the current density of the high-frequency current is relatively high, and the area of the treatment target that is relatively close to the first electrode 31, i.e., the grasp 11, is an area where the current density of the high-frequency current is relatively low. Therefore, as illustrated in FIG. 24A, according to the first temperature distribution, an area S13 of the treatment target where the temperature is relatively high is positioned in an area relatively close to the second electrode 32, i.e., the grasp 12 as the second grasp, and the area of the treatment target where the temperature is relatively low is positioned in an area relatively close to the first electrode 31, i.e., the grasp 11 as the first grasp. In FIG. 24A, the area S13 where the temperature is relatively high is depicted stippled. In the area S13, the temperature goes higher toward the second electrode 32.

Furthermore, according to the present embodiment, heater heat generated by the heater 41 is applied from the first electrode 31 on the grasp 11 as the first grasp to the treatment target. In the treatment target, the heater heat is transmitted from the grasp 11 side to the grasp 12 side. Therefore, as illustrated in FIG. 24B, according to the second temperature distribution, an area S14 of the treatment target where the temperature is relatively high is positioned in an area relatively close to the first electrode 31, i.e., the grasp 11 as the first grasp, and the area of the treatment target where the temperature is relatively low is positioned in an area relatively close to the grasp 12 as the second grasp. In FIG. 24B, the area S14 where the temperature is relatively high is depicted stippled. In the area S14, the temperature goes higher toward the first electrode 31.

Since the first temperature distribution and the second temperature distribution are developed as described hereinbefore, the area S13 where the temperature is relatively high according to the first temperature distribution is positioned in the area where the temperature is relatively low according to the second temperature distribution, according to the present embodiment. The area S14 where the temperature is relatively high according to the second temperature distribution is positioned in the area where the temperature is relatively low according to the first temperature distribution. In the temperature distribution illustrated in FIG. 25, the range covering the high-temperature area S13 according to the first temperature distribution illustrated in FIG. 24A or the high-temperature area S14 according to the second temperature distribution illustrated in FIG. 24B is depicted stippled. In a case where a treatment is carried out, actually, as indicated by the temperature distribution in FIG. 25, most of the treatment target gripped between the grasps 11 and 12 is in the range covering the high-temperature area S13 according to the first temperature distribution or the high-temperature area S14 according to the second temperature distribution. As the temperature distribution described hereinbefore is developed, in a treatment for sealing a treatment target by simultaneously applying a high-frequency current and heater heat to the treatment target, temperature unevenness is restrained from occurring in the treatment target, resulting in an increased capability for sealing the treatment target such as a blood vessel or the like, according to the present embodiment as with the first embodiment.

Other Modifications

According to the embodiments described hereinbefore, etc., the processor 51 switches the output of electric energy from the power supply device 17 to the energy treatment tool 2 between the sealing mode and the incising mode based on an operation from the operating member 18. However, the disclosed technology is not limited to such details. According to a modification, when an operation is entered through the operating member 18, the processor 51 starts outputting electric energy to the energy treatment tool 2 in the sealing mode. When the impedance of the treatment target and the duration time of the output, etc. satisfy predetermined conditions, the processor 51 finishes the output in the sealing mode and automatically switches to the output in the incising mode.

Figure 26:
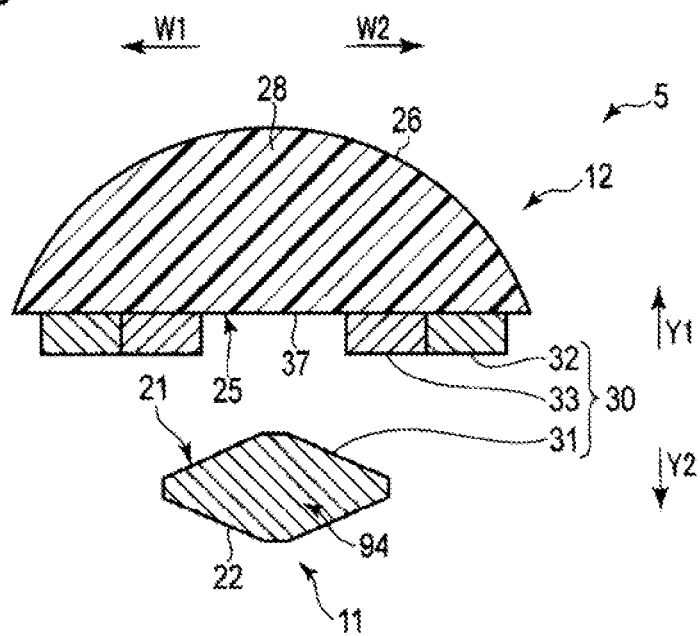
FIG. 26 is a schematic view illustrating a cross section of an end effector according to a modification of the first through fourth embodiments, taken along a plane substantially perpendicular to directions along a longitudinal axis thereof.
Figure 27:
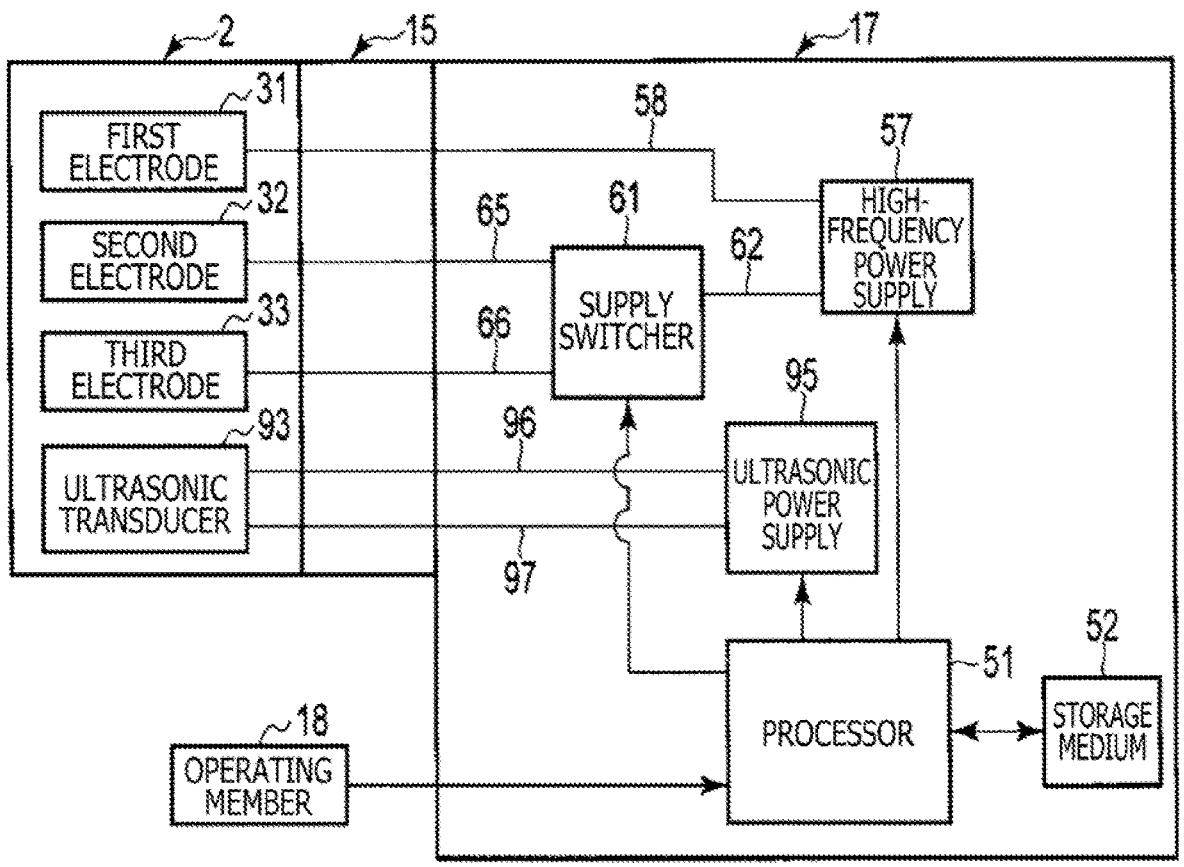
FIG. 27 is a block diagram schematically illustrating an arrangement for controlling the supply of high-frequency electric power to a bipolar electrode and the supply of electric energy to an ultrasonic transducer according to the modification illustrated in FIG. 26.

According to the embodiments described hereinbefore, etc., the heater 41; 41, 72; 41, or 81 is included as the treatment energy source. However, the disclosed technology is not limited to such details. According to a modification illustrated in FIGS. 26 and 27, an ultrasonic transducer 93 is included as a treatment energy source instead of the heater 41; 41, 72; 41, or 81. According to the present modification, the ultrasonic transducer 93 is disposed in the housing 4, for example, and a rod member, i.e., probe 94 is connected to a distal-end side of the ultrasonic transducer 93. The rod member 94 is made of a material of high vibration transmissibility. The rod member 94 is inserted through the shaft 3, for example. A portion of the rod member 94 that projects from the distal end of the shaft 3 toward a distal-end side functions as the grasp 11. According to the present modification, furthermore, the power supply device 17 includes an ultrasonic power supply 95 instead of the heater power supply 53. The ultrasonic power supply 95 is electrically connected to the ultrasonic transducer 93 through electric lines 96 and 97. When electric energy, i.e., AC electric power having a frequency in a predetermined frequency range, is supplied from the ultrasonic power supply 95 to the ultrasonic transducer 93, the ultrasonic transducer 93 generates ultrasonic vibration as treatment energy different from the high-frequency current. The ultrasonic vibration is transmitted to one of the grasps 11 and 12, i.e., the grasp 11 according to the present modification, and applied to a gripped treatment target. At this time, frictional heat is produced between the grasp 11 or 12 to which the ultrasonic vibration is transmitted and the gripped treatment target. The processor 51 controls the output of electric energy from the ultrasonic power supply 95.

According to an embodiment, the overall facing surface 21 of the grasp 11 functions as the first electrode 31, and the second electrode 32 and the third electrode 33 are disposed on the grasp 12 as with the first embodiment. The ultrasonic transducer 93 is included instead of the heater 41. Ultrasonic vibration generated by the ultrasonic transducer 93 is transmitted to the grasp, i.e., first grasp 11 on which the first electrode 31 is disposed. According to the present embodiment, the surface area of the first electrode 31 is larger than the surface area of the second electrode 32 and larger than the surface area of the third electrode 33. The surface area of the first electrode 31 is smaller than the sum of the surface area of the second electrode 32 and the surface area of the third electrode 33. In each of the sealing mode and the incising mode, according to the second temperature distribution developed in the treatment target due to ultrasonic vibration, the area of the treatment target where the temperature is relatively high is positioned in an area relatively close to the first electrode 31, i.e., the grasp 11 as the first grasp, and the area of the treatment target where the temperature is relatively low is positioned in an area relatively close to the grasp 12 as the second grasp. In each of the sealing mode and the incising mode, the first temperature distribution developed in the treatment target due to a high-frequency current is the same as with the first embodiment. According to the present embodiment, therefore, in the sealing mode, the area where the temperature is relatively high according to the first temperature distribution is positioned in an area where the temperature is relatively low according to the second temperature distribution. In the incising mode, the area where the temperature is relatively high according to the second temperature distribution is positioned in an area where the temperature is relatively high according to the first temperature distribution.

According to the embodiments described hereinbefore, etc., when high-frequency electric power is supplied to the bipolar electrode 30, the bipolar electrode 30 causes a high-frequency current to flow through the treatment target between the pair of grasps 11 and 12, developing the first temperature distribution in the treatment target due to the high-frequency current. When electric energy is supplied to the treatment energy source 41; 41, 72; 41, or 81, the treatment energy source 41; 41, 72; 41, or 81 generates treatment energy different from the high-frequency current, and applies the generated treatment energy to the treatment target, developing the second temperature distribution in the treatment target due to the treatment energy. The bipolar electrode 30 and the treatment energy source 41; 41, 72; 41, or 81 are capable of simultaneously applying the high-frequency current and the treatment energy to the treatment target such that the area where the temperature is relatively high according to the first temperature distribution is positioned in the area where the temperature is relatively low according to the second temperature distribution.

The disclosed technology is not limited to the embodiments described hereinbefore, but various modifications may be made therein without departing from the scope of the invention when it is reduced to practice. The embodiments may be appropriately combined as much as possible, and the combinations offer combined advantages. Furthermore, the embodiments include inventions in various stages, and various inventions can be extracted by appropriately combining a plurality of components that are disclosed.

In sum, one aspect of the disclosed technology is directed to a treatment system having respective first and second grasps configured to be coupled with one another and are capable of pivoting with respect to one another so as to grip a treatment target therebetween. A plurality of bipolar electrodes is attached to the respective first and second grasps. The plurality of bipolar electrodes receives high-frequency electric power in a form of a high-frequency current to flow through the treatment target so as to develop a first temperature distribution in the treatment target. A treatment energy source is configured to be coupled to at least one of the respective first and second grasps. The treatment energy source receives electric energy to generate treatment energy different from the high-frequency current and to apply the generated treatment energy to the treatment target so as to develop a second temperature distribution in the treatment target. A processor configured to control transmissions of the respective high-frequency electric power and the electric energy to the respective plurality of bipolar electrodes and the treatment energy source and to switch to a sealing mode and a incising mode. The plurality of bipolar electrodes and the treatment energy source are capable of: in the sealing mode, simultaneously applying the high-frequency current and the treatment energy to the treatment target such that a first area having a relatively high temperature in the first temperature distribution overlaps a second area having a relatively low temperature in the second temperature distribution. And in the incising mode, simultaneously applying the high-frequency current and the treatment energy to the treatment target such that a third area having a relatively high temperature in the first temperature distribution overlaps a fourth area having a relatively high temperature in the second temperature distribution.

The plurality of bipolar electrodes is defined by a first electrode is disposed on the first grasp and a second electrode is disposed on the second grasp. The respective first and second electrodes includes respective first and second surface areas in which the second surface area is different from the first surface area. The plurality of bipolar electrodes further includes a third electrode having a third surface area disposed on the second grasp. The first surface area is larger than each of the respective second and third surface areas and wherein the first surface area is smaller than a sum of the second and third surface areas. The processor is capable of switching the transmission of the high-frequency electric power to the plurality of the bipolar electrodes between the sealing mode and the incising mode. The processor is transmitting high-frequency electric power to the respective first and second electrodes in the sealing mode without transmitting the high-frequency electric power to the third electrode supplies. The processor transmits the high-frequency electric power to the respective first, second, and third electrodes causing the respective second and third electrodes to develop respective potentials that are the same as one another in the incising mode.

The treatment energy source applies the treatment energy from the first grasp to the treatment target and positions the fourth area near the first grasp. The bipolar electrode positions the first area near the second grasp and the bipolar electrode positions the third area near the first grasp. The treatment energy source applies the treatment energy from the second grasp to the treatment target, and positions the fourth area near the second grasp. The bipolar electrode positions the third area near the first grasp and the bipolar electrode positions the first area near the second grasp. The first surface area is larger than the second surface area and the bipolar electrode positions the first area near the second grasp. The processor is capable of switching the supply of the electric energy to the treatment energy source between the sealing mode and the incising mode. The treatment energy source applies the treatment energy from the first grasp to the treatment target in the sealing mode and positions a fourth area near the first grasp. The treatment energy source applies the treatment energy from the second grasp to the treatment target in the incising mode and positions the fourth area near the second grasp. The processor is capable of switching the supply of the high-frequency electric power to the bipolar electrode between the sealing mode and the incising mode. The bipolar electrode positions the first area to the second area in the sealing mode. The bipolar electrode positions the third area to the fourth area in the incising mode. The processor is capable of switching the supply of the electric energy to the treatment energy source between the sealing mode and the incising mode. The treatment energy source positions the fourth area to a fifth area where the temperature is relatively low according to the first temperature distribution in the sealing mode. The treatment energy source positions the fourth area to the third area in the incising mode.

Another aspect of the disclosed technology is directed to an energy treatment tool used in a treatment system having respective first and second grasps configured to be coupled with one another and are capable of pivoting with respect to one another so as to grip a treatment target therebetween. A plurality of bipolar electrodes is attached to the respective first and second grasps. The plurality of bipolar electrodes receives high-frequency electric power in a form of a high-frequency current to flow through the treatment target so as to develop a first temperature distribution in the treatment target. At least one treatment energy source is configured to be coupled to one of the respective first and second grasps. The at least one treatment energy source receives electric energy to generate treatment energy different from the high-frequency current and to apply the generated treatment energy to the treatment target so as to develop a second temperature distribution in the treatment target. The plurality of bipolar electrodes and the treatment energy source are capable of: in a sealing mode, simultaneously applying the high-frequency current and the treatment energy to the treatment target such that a first area having a relatively high temperature in the first temperature distribution overlaps a second area having a relatively low temperature in the second temperature distribution. And in an incising mode, simultaneously applying the high-frequency current and the treatment energy to the treatment target such that a third area having a relatively high temperature in the first temperature distribution overlaps a fourth area having a relatively low temperature in the second temperature distribution.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment system comprising:
respective first and second grasps coupled with one another and being capable of pivoting with respect to one another so as to grip a treatment target therebetween;
a plurality of bipolar electrodes being attached to the respective first and second grasps, the plurality of bipolar electrodes being configured to receive high-frequency electric power in a form of a high-frequency current to flow through the treatment target, so as to develop a first temperature distribution in the treatment target;
a treatment energy source coupled to at least one of the respective first and second grasps, the treatment energy source being configured to receive electric energy to generate treatment energy different from the high-frequency current and to apply the generated treatment energy to the treatment target so as to develop a second temperature distribution in the treatment target; and
a processor configured to control transmissions of the respective high-frequency electric power and the electric energy to the respective plurality of bipolar electrodes and the treatment energy source and to switch to a sealing mode and an incising mode,
wherein:
the plurality of bipolar electrodes and the treatment energy source are configured to:
in the sealing mode, simultaneously apply the high-frequency current and the treatment energy to the treatment target such that a first area having a higher temperature than other areas in the first temperature distribution overlaps a second area having a lower temperature than other areas in the second temperature distribution, and
in the incising mode, simultaneously apply the high-frequency current and the treatment energy to the treatment target such that a third area having a higher temperature than other areas in the first temperature distribution overlaps a fourth area having a higher temperature than other areas in the second temperature distribution, the plurality of bipolar electrodes includes a first electrode disposed on the first grasp and a second electrode disposed on the second grasp,
the respective first and second electrodes include respective first and second surface areas,
the second surface area is different from the first surface area,
the plurality of bipolar electrodes further includes a third electrode having a third surface area disposed on the second grasp,
the first surface area is larger than each of the respective second and third surface areas, and
the first surface area is smaller than a sum of the second and third surface areas.

2. The treatment system of claim 1, wherein
the processor is capable of switching the transmission of the high-frequency electric power to the plurality of the bipolar electrodes between the sealing mode and the incising mode, and
the processor is configured to:
  transmit high-frequency electric power to the respective first and second electrodes in the sealing mode without transmitting the high-frequency electric power to the third electrode, and
  transmit the high-frequency electric power to the respective first, second, and third electrodes causing the respective second and third electrodes to develop respective potentials that are the same as one another in the incising mode.

3. The treatment system of claim 2, wherein
the treatment energy source is configured to apply the treatment energy from the first grasp to the treatment target and position the fourth area near the first grasp, and
one or more of the bipolar electrodes are configured to:
  position the first area near the second grasp, and
  position the third area near the first grasp.

4. The treatment system of claim 2, wherein
the treatment energy source is configured to apply the treatment energy from the second grasp to the treatment target, and position the fourth area near the second grasp, and
one or more of positions electrodes are configured to:
  position the third area near the first grasp, and
  position the first area near the second grasp.

5. The treatment system of claim 1, wherein
the first surface area is larger than the second surface area, and
one or more of positions electrodes are configured to position the first area near the second grasp.

6. The treatment system of claim 5, wherein
the processor is capable of switching the supply of the electric energy to the treatment energy source between the sealing mode and the incising mode, and
the treatment energy source is configured to:
  apply the treatment energy from the first grasp to the treatment target in the sealing mode, and position a fourth area near the first grasp, and
  apply the treatment energy from the second grasp to the treatment target in the incising mode, and position the fourth area near the second grasp.

7. The treatment system of claim 1, wherein
the processor is capable of switching the supply of the high-frequency electric power to the bipolar electrode between the sealing mode and the incising mode; and
one or more of the bipolar positions electrodes are configured to:
  position the first area to the second area in the sealing mode, and
  position the third area to the fourth area in the incising mode.

8. The treatment system of claim 1, wherein
the processor is capable of switching the supply of the electric energy to the treatment energy source between the sealing mode and the incising mode, and
the treatment energy source is configured to:
  position the fourth area to a fifth area where the temperature is lower than other areas according to the first temperature distribution in the sealing mode, and
  position the fourth area to the third area in the incising mode.

9. An energy treatment tool used in a treatment system comprising:
respective first and second grasps coupled with one another and of pivoting with respect to one another so as to grip a treatment target therebetween;
a plurality of bipolar electrodes being attached to the respective first and second grasps, the plurality of bipolar electrodes being configured to receive high-frequency electric power in a form of a high-frequency current to flow through the treatment target, so as to develop a first temperature distribution in the treatment target; and
a treatment energy source coupled to at least one of the respective first and second grasps, the at least one treatment energy source being configured to receive electric energy to generate treatment energy different from the high-frequency current and to apply the generated treatment energy to the treatment target so as to develop a second temperature distribution in the treatment target,
wherein:
  the plurality of bipolar electrodes and the treatment energy source are configured to:
    in a sealing mode, simultaneously apply the high-frequency current and the treatment energy to the treatment target such that a first area having a higher temperature than other areas in the first temperature distribution overlaps a second area having a lower temperature than other areas in the second temperature distribution, and
    in an incising mode, simultaneously apply the high-frequency current and the treatment energy to the treatment target such that a third area having a higher temperature than other areas in the first temperature distribution overlaps a fourth area having a lower temperature than other areas in the second temperature distribution,
  the plurality of bipolar electrodes includes a first electrode disposed on the first grasp and a second electrode disposed on the second grasp,
  the respective first and second electrodes include respective first and second surface areas,
  the second surface area is different from the first surface area,
  the plurality of bipolar electrodes further includes a third electrode having a third surface area disposed on the second grasp,
  the first surface area is larger than each of the respective second and third surface areas, and
  the first surface area is smaller than a sum of the second and third surface areas.

10. A treatment system comprising:
respective first and second grasps coupled with one another and of pivoting with respect to one another so as to grip a treatment target therebetween;
a plurality of bipolar electrodes being attached to the respective first and second grasps, the plurality of bipolar electrodes being configured to receive high-frequency electric power in a form of a high-frequency current to flow through the treatment target, so as to develop a first temperature distribution in the treatment target;
a treatment energy source coupled to at least one of the respective first and second grasps, the treatment energy source being configured to receive electric energy to generate treatment energy different from the high-frequency current and to apply the generated treatment energy to the treatment target so as to develop a second temperature distribution in the treatment target; and
a processor configured to control transmissions of the respective high-frequency electric power and the electric energy to the respective plurality of bipolar electrodes and the treatment energy source and to switch to a sealing mode and an incising mode,
wherein:
the plurality of bipolar electrodes and the treatment energy source are configured to:
in the sealing mode, simultaneously apply the high-frequency current and the treatment energy to the treatment target such that a first area having a higher temperature than other areas in the first temperature distribution overlaps a second area having a lower temperature than other areas in the second temperature distribution, and
in the incising mode, simultaneously apply the high-frequency current and the treatment energy to the treatment target such that a third area having a higher temperature than other areas in the first temperature distribution overlaps a fourth area having a higher temperature than other areas in the second temperature distribution; and
the processor is capable of switching the supply of the electric energy to the treatment energy source between the sealing mode and the incising mode, and the treatment energy source is configured to:
position the fourth area to a fifth area where the temperature is lower than other areas according to the first temperature distribution in the sealing mode, and
position the fourth area to the third area in the incising mode.

11. The treatment system of claim 10, wherein
the plurality of bipolar electrodes is defined by a first electrode is disposed on the first grasp and a second electrode is disposed on the second grasp,
the respective first and second electrodes include respective first and second surface areas, and
the second surface area is different from the first surface area.

12. The treatment system of claim 11, wherein
the first surface area is larger than the second surface area, and
one or more the bipolar electrodes are configured to position the first area near the second grasp.

13. The treatment system of claim 12, wherein
the processor is capable of switching the supply of the electric energy to the treatment energy source between the sealing mode and the incising mode, and
the treatment energy source is configured to:
apply the treatment energy from the first grasp to the treatment target in the sealing mode, and position the fourth area near the first grasp, and
apply the treatment energy from the second grasp to the treatment target in the incising mode, and position the fourth area near the second grasp.

14. The treatment system of claim 10, wherein
the processor is capable of switching the supply of the high-frequency electric power to between the sealing mode and the incising mode; and
one or more of the bipolar electrodes are configured to:
position the first area to the second area in the sealing mode, and
position the third area to the fourth area in the incising mode.

* * * * *